United States Patent
Wu et al.

(10) Patent No.: US 10,591,436 B2
(45) Date of Patent: Mar. 17, 2020

(54) RESIDUAL COMPENSATION INCLUDING UNDERFILL ERROR

(75) Inventors: Huan-Ping Wu, Granger, IN (US); Bern Harrison, Granger, IN (US); Eric Maurer, South Bend, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 1974 days.

(21) Appl. No.: 13/053,722

(22) Filed: Mar. 22, 2011

(65) Prior Publication Data

US 2011/0231105 A1    Sep. 22, 2011

Related U.S. Application Data

(60) Provisional application No. 61/316,174, filed on Mar. 22, 2010.

(51) Int. Cl.
*G06F 19/00* (2018.01)
*G01N 27/327* (2006.01)

(52) U.S. Cl.
CPC .............................. *G01N 27/3274* (2013.01)

(58) Field of Classification Search
CPC ............ G05B 23/0235; G05B 23/0243; G05B 23/0254; G05B 23/0286; G05B 23/0294; C12Q 2537/165; C12Q 2545/101; C12Q 2454/114; G06F 19/24; G06F 17/18; G01N 27/3274; G01N 21/274; G01N 27/327; G01N 27/4163; G01N 33/48771; G01N 21/359; G01N 21/65; G01N 21/658; A61K 47/26; G16B 20/00; G16B 30/00; G16B 40/00; G16B 30/10; G16B 20/10; G16B 25/00; G16H 50/20; C40B 30/06; A61B 5/0075; G02B 21/0004

See application file for complete search history.

(56) References Cited

U.S. PATENT DOCUMENTS

| | | |
|---|---|---|
| 4,431,004 A | 2/1984 | Bessman et al. |
| 4,750,496 A | 6/1988 | Reinhart et al. |
| (Continued) | | |

FOREIGN PATENT DOCUMENTS

| | | |
|---|---|---|
| EP | 1 422 523 A1 | 5/2004 |
| EP | 1742045 | 1/2007 |
| (Continued) | | |

OTHER PUBLICATIONS

Zeng, Q. C. et al. 2008, Analyst vol. 133, pp. 1649-1655.*

(Continued)

*Primary Examiner* — Mary K Zeman
(74) *Attorney, Agent, or Firm* — Nixon Peabody LLP

(57) ABSTRACT

A biosensor system determines analyte concentration from an output signal generated from a light-identifiable species or a redox reaction of the analyte. The biosensor system compensates at least 50% of the total error in the output signal with a primary function and compensates a portion of the remaining error with a residual function. The amount of error compensation provided by the primary and residual functions may be adjusted with a weighing coefficient. The compensation method including a primary function and a residual function may be used to determine analyte concentrations having improved accuracy from output signals including components attributable to error.

15 Claims, 16 Drawing Sheets

(56) References Cited

U.S. PATENT DOCUMENTS

| | | |
|---|---|---|
| 5,243,516 A | 9/1993 | White |
| 5,352,351 A | 10/1994 | White et al. |
| 5,366,609 A | 11/1994 | White et al. |
| 5,395,504 A | 3/1995 | Saurer et al. |
| 5,508,171 A | 4/1996 | Walling et al. |
| 5,582,697 A | 12/1996 | Ikeda et al. |
| 5,620,579 A | 4/1997 | Genshaw et al. |
| 5,653,863 A | 8/1997 | Genshaw et al. |
| 5,723,284 A | 3/1998 | Ye |
| 5,798,031 A | 8/1998 | Charlton et al. |
| 6,120,676 A | 9/2000 | Heller et al. |
| 6,153,069 A | 11/2000 | Pottgen et al. |
| 6,233,471 B1 | 5/2001 | Berner et al. |
| 6,275,717 B1 | 8/2001 | Gross et al. |
| 6,391,645 B1 | 5/2002 | Huang et al. |
| 6,413,411 B1 | 7/2002 | Pottgen et al. |
| 6,448,067 B1 | 9/2002 | Tajnafoi |
| 6,475,372 B1 | 11/2002 | Ohara et al. |
| 6,531,040 B2 | 3/2003 | Musho et al. |
| 6,576,117 B1 | 6/2003 | Iketaki et al. |
| 6,645,368 B1 | 11/2003 | Beaty et al. |
| 6,797,150 B2 | 9/2004 | Kermani et al. |
| 6,824,670 B2 | 11/2004 | Tokunaga et al. |
| 7,118,668 B1 | 10/2006 | Edelbrock et al. |
| 7,122,110 B2 | 10/2006 | Deng et al. |
| 7,122,111 B2 | 10/2006 | Tokunaga et al. |
| 7,132,041 B2 | 11/2006 | Deng et al. |
| 7,195,704 B2 | 3/2007 | Kermani et al. |
| 7,351,323 B2 | 4/2008 | Iketaki et al. |
| 7,488,601 B2 | 2/2009 | Burke et al. |
| 7,491,310 B2 | 2/2009 | Okuda et al. |
| 7,501,052 B2 | 3/2009 | Iyenga et al. |
| 7,517,439 B2 | 4/2009 | Harding et al. |
| 7,822,557 B2 | 10/2010 | Deng |
| 7,966,859 B2 | 6/2011 | Wu et al. |
| 8,002,965 B2 | 8/2011 | Beer et al. |
| 8,088,272 B2 | 1/2012 | Deng |
| 8,101,062 B2 | 1/2012 | Deng |
| 2002/0084196 A1 | 7/2002 | Liamos et al. |
| 2002/0146835 A1 | 10/2002 | Modzelewski et al. |
| 2002/0160517 A1 | 10/2002 | Modzelewski et al. |
| 2004/0072158 A1 | 4/2004 | Henkens et al. |
| 2004/0079652 A1 | 4/2004 | Vreke et al. |
| 2004/0256248 A1 | 12/2004 | Burke et al. |
| 2004/0260511 A1 | 12/2004 | Burke et al. |
| 2005/0023154 A1 | 2/2005 | Kermani et al. |
| 2005/0176153 A1 | 8/2005 | O'hara et al. |
| 2007/0231914 A1 | 10/2007 | Deng et al. |
| 2008/0000780 A1 | 1/2008 | Tonks |
| 2008/0173552 A1 | 7/2008 | Wu et al. |
| 2008/0179197 A1 | 7/2008 | Wu |
| 2008/0248581 A1 | 10/2008 | Chu et al. |
| 2009/0023222 A1 | 1/2009 | Wu |
| 2009/0099787 A1 | 4/2009 | Carpenter et al. |
| 2009/0177406 A1* | 7/2009 | Wu .................................. 702/19 |
| 2011/0297554 A1 | 12/2011 | Wu et al. |
| 2011/0301857 A1 | 12/2011 | Huang et al. |

FOREIGN PATENT DOCUMENTS

| | | |
|---|---|---|
| JP | 2005-040267 | 2/2005 |
| JP | 2005147990 | 6/2005 |
| JP | 2009-528540 | 8/2009 |
| RU | 2 050 545 C1 | 12/1995 |
| RU | 2 135 993 C1 | 8/1999 |
| RU | 2 194 987 C2 | 12/2002 |
| RU | 2 241 985 | 12/2004 |
| WO | 1996014026 | 10/1995 |
| WO | 1998058250 | 12/1998 |
| WO | 2001021827 | 3/2001 |
| WO | 2003091717 | 4/2003 |
| WO | 2006042304 | 4/2005 |
| WO | 2005073393 | 8/2005 |
| WO | 2005078437 | 8/2005 |
| WO | WO 2005/103669 A1 | 11/2005 |
| WO | 2006079797 | 8/2006 |
| WO | 2007040913 | 4/2007 |
| WO | WO 2007/132903 A1 | 11/2007 |
| WO | 2009108239 | 9/2009 |
| WO | 2010077660 | 7/2010 |
| WO | 2011059670 | 5/2011 |

OTHER PUBLICATIONS

Anzenbacher, Jr. P. et al. Sep. 2010 A practical approach to optical cross-reactive sensor arrays, Chemical Society Reviews, vol. 39, pp. 3954-3979.*

Panteleon, et al., "The Role of the Independent Variable to Gluscose Sensor Calibration", "Diabetes Technology & Therapeutics", 2003, pp. 401-441, vol. 5, No. 3.

International Searching Authority, "International Search Report and Written Opinion for PCT/US2006/028013", dated Dec. 6, 2006, Publisher: European Patent Office, Published in: EP.

International Searching Authority, "International Search Report and Written Opinion for PCT/US2007/068320", dated Oct. 19, 2007, Publisher: European Patent Office, Published in: EP.

International Searching Authority, "International Search Report and Written Opinion for PCT/US2008/085768", dated Sep. 28, 2009, Publisher: European Patent Office, Published in: EP.

International Searching Authority, "International Search Report and Written Opinion for PCT/US2011/029318", dated Jun. 20, 2011, Publisher: European Patent Office.

Gunasingham, et al., "Pulsed amperometric detection of glucose using a mediated enzyme electrode", "Journal of Electroanalytical Chemisty", 1990, pp. 349-362, vol. 287, No. 2.

Lin, et al., "Reduction of the Interferences of Biochemicals and Hematrocrit Ratio on the Determination of Whole Blood Glucose Using", "Anal. Bioanal. Chem.", 2007, pp. 1623-1631, vol. 289.

Agamatrix, Inc. , "Wavesense. How It Works.", May 30, 2008, Publisher: http://www.wavesense.info/how-it-works.

* cited by examiner

RESIDUAL COMPENSATION INCLUDING UNDERFILL ERROR

REFERENCE TO RELATED APPLICATIONS

This application claims the benefit of U.S. Provisional Application No. 61/316,174 entitled "Residual Compensation Including Underfill" filed Mar. 22, 2010, which is incorporated by reference in its entirety.

BACKGROUND

Biosensor systems provide an analysis of a biological fluid sample, such as whole blood, serum, plasma, urine, saliva, interstitial, or intracellular fluid. Typically, the systems include a measurement device that analyzes a sample residing in a test sensor. The sample usually is in liquid form and in addition to being a biological fluid, may be the derivative of a biological fluid, such as an extract, a dilution, a filtrate, or a reconstituted precipitate. The analysis performed by the biosensor system determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. The analysis may be useful in the diagnosis and treatment of physiological abnormalities. For example, a diabetic individual may use a biosensor system to determine the glucose level in whole blood for adjustments to diet and/or medication.

Biosensor systems may be designed to analyze one or more analytes and may use different volumes of biological fluids. Some systems may analyze a single drop of whole blood, such as from 0.25-15 microliters (μL) in volume. Biosensor systems may be implemented using bench-top, portable, and like measurement devices. Portable measurement devices may be hand-held and allow for the identification and/or quantification of one or more analytes in a sample. Examples of portable measurement systems include the Elite® meters of Bayer HealthCare in Tarrytown, N.Y., while examples of bench-top measurement systems include the Electrochemical Workstation available from CH Instruments in Austin, Tex.

Biosensor systems may use optical and/or electrochemical methods to analyze the biological fluid. In some optical systems, the analyte concentration is determined by measuring light that has interacted with or been absorbed by a light-identifiable species, such as the analyte or a reaction or product formed from a chemical indicator reacting with the analyte. In other optical systems, a chemical indicator fluoresces or emits light in response to the analyte when illuminated by an excitation beam. The light may be converted into an electrical output signal, such as current or potential, which may be similarly processed to the output signal from an electrochemical system. In either optical system, the system measures and correlates the light with the analyte concentration of the sample.

In light-absorption optical systems, the chemical indicator produces a reaction product that absorbs light. A chemical indicator such as tetrazolium along with an enzyme such as diaphorase may be used. Tetrazolium usually forms formazan (a chromagen) in response to the redox reaction of the analyte. An incident input beam from a light source is directed toward the sample. The light source may be a laser, a light emitting diode, or the like. The incident beam may have a wavelength selected for absorption by the reaction product. As the incident beam passes through the sample, the reaction product absorbs a portion of the incident beam, thus attenuating or reducing the intensity of the incident beam. The incident beam may be reflected back from or transmitted through the sample to a detector. The detector collects and measures the attenuated incident beam (output signal). The amount of light attenuated by the reaction product is an indication of the analyte concentration in the sample.

In light-generated optical systems, the chemical detector fluoresces or emits light in response to the analyte redox reaction. A detector collects and measures the generated light (output signal). The amount of light produced by the chemical indicator is an indication of the analyte concentration in the sample.

In electrochemical biosensor systems, the analyte concentration is determined from an electrical signal generated by an oxidation/reduction or redox reaction of the analyte or a species responsive to the analyte when an input signal is applied to the sample. The input signal may be a potential or current and may be constant, variable, or a combination thereof such as when an AC signal is applied with a DC signal offset. The input signal may be applied as a single pulse or in multiple pulses, sequences, or cycles. An enzyme or similar species may be added to the sample to enhance the electron transfer from a first species to a second species during the redox reaction. The enzyme or similar species may react with a single analyte, thus providing specificity to a portion of the generated output signal. A mediator may be used to maintain the oxidation state of the enzyme and/or assist with electron transfer from the analyte to an electrode.

Electrochemical biosensor systems usually include a measurement device having electrical contacts that connect with the electrical conductors of the test sensor. The conductors may be made from conductive materials, such as solid metals, metal pastes, conductive carbon, conductive carbon pastes, conductive polymers, and the like. The electrical conductors typically connect to working, counter, reference, and/or other electrodes that extend into a sample reservoir. One or more electrical conductors also may extend into the sample reservoir to provide functionality not provided by the electrodes.

The measurement device applies an input signal through the electrical contacts to the electrical conductors of the test sensor. The electrical conductors convey the input signal through the electrodes into the sample present in the sample reservoir. The redox reaction of the analyte generates an electrical output signal in response to the input signal. The electrical output signal from the test sensor may be a current (as generated by amperometry or voltammetry), a potential (as generated by potentiometry/galvanometry), or an accumulated charge (as generated by coulometry). The measurement device may have the processing capability to measure and correlate the output signal with the presence and/or concentration of one or more analytes in the sample.

In coulometry, a potential is applied to the sample to exhaustively oxidize or reduce the analyte. A biosensor system using coulometry is described in U.S. Pat. No. 6,120,676. In amperometry, an electrical signal of constant potential (voltage) is applied to the electrical conductors of the test sensor while the measured output signal is a current. Biosensor systems using amperometry are described in U.S. Pat. Nos. 5,620,579; 5,653,863; 6,153,069; and 6,413,411. In voltammetry, an electric signal of varying potential is applied to a sample of biological fluid, while the measured output is current. In gated amperometry and gated voltammetry, pulsed inputs are used as described in WO 2007/013915 and WO 2007/040913, respectively.

In many biosensor systems, the test sensor may be adapted for use outside, inside, or partially inside a living organism. When used outside a living organism, a sample of the biological fluid may be introduced into a sample reservoir in the test sensor. The test sensor may be placed in the measurement device before, after, or during the introduction of the sample for analysis. When inside or partially inside a living organism, the test sensor may be continually immersed in the sample or the sample may be intermittently introduced to the test sensor. The test sensor may include a reservoir that partially isolates a volume of the sample or be open to the sample. When open, the test sensor may take the form of a fiber or other structure placed in contact with the biological fluid. Similarly, the sample may continuously flow through the test sensor, such as for continuous monitoring, or be interrupted, such as for intermittent monitoring, for analysis.

The measurement performance of a biosensor system is defined in terms of accuracy, which reflects the combined effects of random and systematic error components. Systematic error, or trueness, is the difference between the average value determined from the biosensor system and one or more accepted reference values for the analyte concentration of the biological fluid. Trueness may be expressed in terms of mean bias, with larger mean bias values representing lower trueness and thereby contributing to less accuracy. Precision is the closeness of agreement among multiple analyte readings in relation to a mean. One or more errors in the analysis contribute to the bias and/or imprecision of the analyte concentration determined by the biosensor system. A reduction in the analysis error of a biosensor system therefore leads to an increase in accuracy and thus an improvement in measurement performance.

Bias may be expressed in terms of "absolute bias" or "percent bias". Absolute bias may be expressed in the units of the measurement, such as mg/dL, while percent bias may be expressed as a percentage of the absolute bias value over 100 mg/dL or the reference analyte concentration of the sample. For glucose concentrations less than 100 mg/dL, percent bias is defined as (the absolute bias over 100 mg/dL)*100. For glucose concentrations of 100 mg/dL and higher, percent bias is defined as the absolute bias over the reference analyte concentration*100. Accepted reference values for the analyte glucose in whole blood samples may be obtained with a reference instrument, such as the YSI 2300 STAT PLUS™ available from YSI Inc., Yellow Springs, Ohio. Other reference instruments and ways to determine percent bias may be used for other analytes.

Hematocrit bias refers to the average difference (systematic error) between the reference glucose concentration obtained with a reference instrument and experimental glucose readings obtained from a biosensor system for samples containing differing hematocrit levels. The difference between the reference and values obtained from the system results from the varying hematocrit level between specific whole blood samples and may be generally expressed as a percentage by the following equation: % Hct-Bias=100%× $(G_m-G_{ref})/G_{ref}$, where $G_m$ is the determined glucose concentration at a specific hematocrit level and $G_{ref}$ is the reference glucose concentration at a reference hematocrit level. The larger the absolute value of the % Hct-bias, the more the hematocrit level of the sample (expressed as % Hct, the percentage of red blood cell volume/sample volume) is reducing the accuracy of the determined glucose concentration.

For example, if whole blood samples containing identical glucose concentrations, but having hematocrit levels of 20, 40, and 60%, are analyzed, three different glucose concentrations will be reported by a system based on one set of calibration constants (slope and intercept of the 40% hematocrit containing whole blood sample, for instance). Thus, even though the whole blood glucose concentrations are the same, the system will report that the 20% hematocrit sample contains more glucose than the 40% hematocrit sample, and that the 60% hematocrit sample contains less glucose than the 40% hematocrit sample. "Hematocrit sensitivity" is an expression of the degree to which changes in the hematocrit level of a sample affect the bias values for an analysis. Hematocrit sensitivity may be defined as the numerical values of the percent biases per percent hematocrit, thus bias/%-bias per % Hct.

Biosensor systems may provide an output signal during the analysis of the biological fluid that includes errors from multiple error sources. These error sources contribute to the total error, which may be reflected in an abnormal output signal, such as when one or more portions or the entire output signal is non-responsive or improperly responsive to the analyte concentration of the sample.

These errors may be from one or more contributors, such as the physical characteristics of the sample, the environmental aspects of the sample, the operating conditions of the system, the manufacturing variation between test sensor lots, and the like. Physical characteristics of the sample include hematocrit (red blood cell) concentration, interfering substances, such as lipids and proteins, and the like. Interfering substances include ascorbic acid, uric acid, acetaminophen, and the like. Environmental aspects of the sample include temperature and the like. Operating conditions of the system include underfill conditions when the sample size is not large enough, slow-filling of the sample, intermittent electrical contact between the sample and one or more electrodes in the test sensor, prior degradation of the reagents that interact with the analyte, and the like. Manufacturing variations between test sensor lots include changes in the amount and/or activity of the reagents, changes in the electrode area and/or spacing, changes in the electrical conductivity of the conductors and electrodes, and the like. A test sensor lot is preferably made in a single manufacturing run where lot-to-lot manufacturing variation is substantially reduced or eliminated. Manufacturing variations also may be introduced as the activity of the reagents changes or degrades between the time the test sensor is manufactured and when it is used for an analysis. There may be other contributors or a combination of contributors that cause errors in the analysis.

Percent bias limit, percent bias standard deviation, average percent bias standard deviation, mean percent bias spread, and hematocrit sensitivity are independent ways to express the measurement performance of a biosensor system. Additional ways may be used to express the measurement performance of a biosensor system.

Percent bias limits are a representation of the accuracy of the biosensor system in relation to a reference analyte concentration, while the percent bias standard deviation and average percent bias standard deviation reflect the precision achieved across multiple test sensors of a single or of multiple manufacturing lots, respectively, with regard to errors arising from the physical characteristics of the sample, the environmental aspects of the sample, and the operating conditions of the system. Mean percent bias spread (the distance of the mean percent bias of a single lot from the mean of the mean percent bias of two or more test sensor lots) reflects the closeness of the analyte concentrations determined from the test sensors of two or more test sensor lots for the same analyte concentration in view of the manufacturing variation between the lots.

The percent of analyses that fall within a "percent bias limit" of a selected percent bias boundary indicate the percent of the determined analyte concentrations that are close to a reference concentration. Thus, the limit defines how close the determined analyte concentrations are to the reference concentration. For instance, 95 out of 100 performed analysis (95%) falling within a ±10% percent bias limit is a more accurate result than 80 out of 100 performed analysis (80%) falling within a ±10% percent bias limit. Thus, an increase in the percentage of analyses falling within a selected percent bias limit represents an increase in the measurement performance of the biosensor system.

The mean may be determined for the percent biases determined from multiple analyses using test sensors from a single lot to provide a "mean percent bias" for the multiple analyses. The mean percent bias may be determined for a single lot of test sensors by using a subset of the lot, such as 100-140 test sensors, to analyze multiple blood samples. As a mean percent bias may be determined for a single lot of test sensors, a "percent bias standard deviation" also may be determined to describe how far the percent bias from an individual analysis is away from the mean percent bias of the test sensor lot. Percent bias standard deviation may be considered an indicator of the precision of a single analysis in relation to the mean of multiple analyses from the same test sensor lot. These percent bias standard deviation values may be averaged, such as arithmetically, using root mean squares, or by other means, to provide an indicator of the precision of a single analysis in relation to the mean of multiple analyses from multiple test sensor lots. Thus, a decrease in percent bias standard deviation or the average percent bias standard deviation represents an increase in the measurement performance of the biosensor system in relation to a single test sensor lot or multiple test sensor lots, respectively.

The mean may be determined for the mean percent biases determined from multiple analyses using test sensors from multiple lots to provide a "grand mean percent bias" for the multiple lots. The grand mean percent bias may be determined for two or more lots of test sensors. As a grand mean percent bias may be determined for multiple lots of test sensors, a "mean percent bias spread" also may be determined to describe how far the mean percent bias from an individual test sensor lot is away from the grand mean percent bias of multiple test sensor lots. Mean percent bias spread may be considered an indicator of the precision of a single test sensor lot in relation to the mean of the mean of multiple analyses from multiple test sensor lots. Thus, a decrease in mean percent bias spread represents an increase in the measurement performance of the biosensor system in relation to manufacturing variations from multiple test sensor lots and an increase in the precision achieved across multiple test sensors from multiple manufacturing lots with regard to errors arising from the manufacturing variation between the lots.

Increasing the measurement performance of the biosensor system by reducing errors from these or other sources means that more of the analyte concentrations determined by the biosensor system may be used for accurate therapy by the patient when blood glucose is being monitored, for example. Additionally, the need to discard test sensors and repeat the analysis by the patient also may be reduced.

A test case is a collection of multiple analyses (data population) arising under substantially the same testing conditions using test sensors from the same lot. For example, determined analyte concentration values have typically exhibited poorer measurement performance for user self-testing than for health care professional ("HCP") testing and poorer measurement performance for HCP-testing than for controlled environment testing. This difference in measurement performance may be reflected in larger percent bias standard deviations for analyte concentrations determined through user self-testing than for analyte concentrations determined through HCP-testing or through controlled environment testing. A controlled environment is an environment where physical characteristics and environmental aspects of the sample may be controlled, preferably a laboratory setting. Thus, in a controlled environment, hematocrit concentrations can be fixed and actual sample temperatures can be known and compensated. In a HCP test case, operating condition errors may be reduced or eliminated. In a user self-testing test case, such as a clinical trial, the determined analyte concentrations likely will include error from all types of error sources.

Biosensor systems may have a single source of uncorrected output values responsive to a redox or light-based reaction of the analyte, such as the counter and working electrodes of an electrochemical system. Biosensor systems also may have the optional ability to determine or estimate temperature, such as with one or more thermocouples or other means. In addition to these systems, biosensor systems also may have the ability to generate additional output values external to those from the analyte or from a mediator responsive to the analyte. For example, in an electrochemical test sensor, one or more electrical conductors also may extend into the sample reservoir to provide functionality not provided by the working and counter electrodes. Such conductors may lack one or more of the working electrode reagents, such as the mediator, thus allowing for the subtraction of a background interferent signal from the working electrode signal.

Many biosensor systems include one or more methods to compensate for errors associated with an analysis, thus attempting to improve the measurement performance of the biosensor system. Compensation methods may increase the measurement performance of a biosensor system by providing the biosensor system with the ability to compensate for inaccurate analyses, thus increasing the accuracy and/or precision of the concentration values obtained from the system. Conventional error compensation methods for physical and environmental error contributors are traditionally developed in a laboratory as these types of errors can be reproduced in a controlled environment. However, operating condition error contributors are less readily reproduced in the laboratory as many of these errors arise from the way in which the user operates the biosensor system. Thus, errors arising from operating errors may be difficult to reproduce in a laboratory setting and thus difficult to compensate with a conventional compensation method.

Accordingly, there is an ongoing need for improved biosensor systems, especially those that may provide increasingly accurate determination of sample analyte concentrations when operating condition errors are introduced into the analysis by user self-testing. The systems, devices, and methods of the present invention overcome at least one of the disadvantages associated with conventional biosensor systems.

SUMMARY

In one aspect, the invention provides a method for determining an analyte concentration in a sample that includes generating an output signal responsive to a concentration of the analyte in the sample and an input signal; compensating the output signal with a primary function and a first residual function to determine a compensated output signal; and determining the analyte concentration in the sample from the compensated output signal. A conversion function may be used to convert the output signal to an uncompensated output signal prior to compensating the output signal. The uncompensated output signal may be an uncompensated analyte concentration value.

In another aspect of the invention, there is a method of determining an analyte concentration in a sample that includes generating an output signal responsive to a concentration of an analyte in a sample and an input signal, determining a compensated output signal from the output signal in response to a primary function and a first residual function, and determining the analyte concentration in the sample from the compensated output signal. The primary function may include an index function or a complex index function and preferably corrects errors arising from hematocrit levels in whole blood samples and from temperature.

In another aspect of the invention, there is a method of determining a residual function that includes selecting multiple error parameters as potential terms in the first residual function, determining a first exclusion value for the potential terms, applying an exclusion test responsive to the first exclusion value for the potential terms to identify one or more of the potential terms for exclusion from the first residual function, and excluding one or more identified potential terms from the first residual function.

In another aspect of the invention, there is a biosensor system for determining an analyte concentration in a sample that includes a test sensor having a sample interface in electrical communication with a reservoir formed by the sensor and a measurement device having a processor connected to a sensor interface through a signal generator, the sensor interface having electrical communication with the sample interface, and the processor having electrical communication with a storage medium. The processor instructs the signal generator to apply an electrical input signal to the sensor interface, determines an output signal value responsive to the concentration of the analyte in the sample from the sensor interface, and compensates at least 50% of the total error in the output signal value with a primary function. The processor also compensates at least 5% of the remaining error in the output signal value with a first residual function, the first residual function previously stored in the storage medium, to determine a compensated value, and determines the analyte concentration in the sample from the compensated value. The measurement device of the biosensor system is preferably portable.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

Analysis errors and the resultant bias in determined analyte concentrations may be reduced through the compensation of residual errors. By focusing on the residual errors and finding residual functions associated with the residual errors, the total error in the analysis may be reduced. The errors from the biosensor system may have multiple error sources or contributors arising from different processes/behaviors that are partially or wholly independent. By compensating primary errors, such as temperature and hematocrit, with a primary compensation function to remove at least 50% of the total error, the remaining residual errors may be determined, and a residual function associated with these residual errors may be determined.

Residual error compensation may substantially compensate for the total errors in an analysis until the errors become random. Random errors are those that are not attributed to any error contributor and not described by a residual function at a level considered to be statistically significant. Compensation from primary and residual functions in combination may improve the measurement performance of the biosensor system in more than one way. For example, the combined primary and residual compensation may improve the measurement performance of the biosensor system with regard to one or more of a percent bias limit, a percent bias standard deviation, an average percent bias standard deviation, a mean percent bias spread, and/or in other ways.

Residual error compensation may provide the greatest benefit to samples analyzed by users themselves during "self-testing". Residual error compensation also may provide benefit to samples analyzed by a health care professional (HCP). While not wishing to be bound by any particular theory, it is believed that self-testing errors can originate from different behaviors or processes that are substantially independent of controlled environment or HCP-testing errors.

Figure 1A:
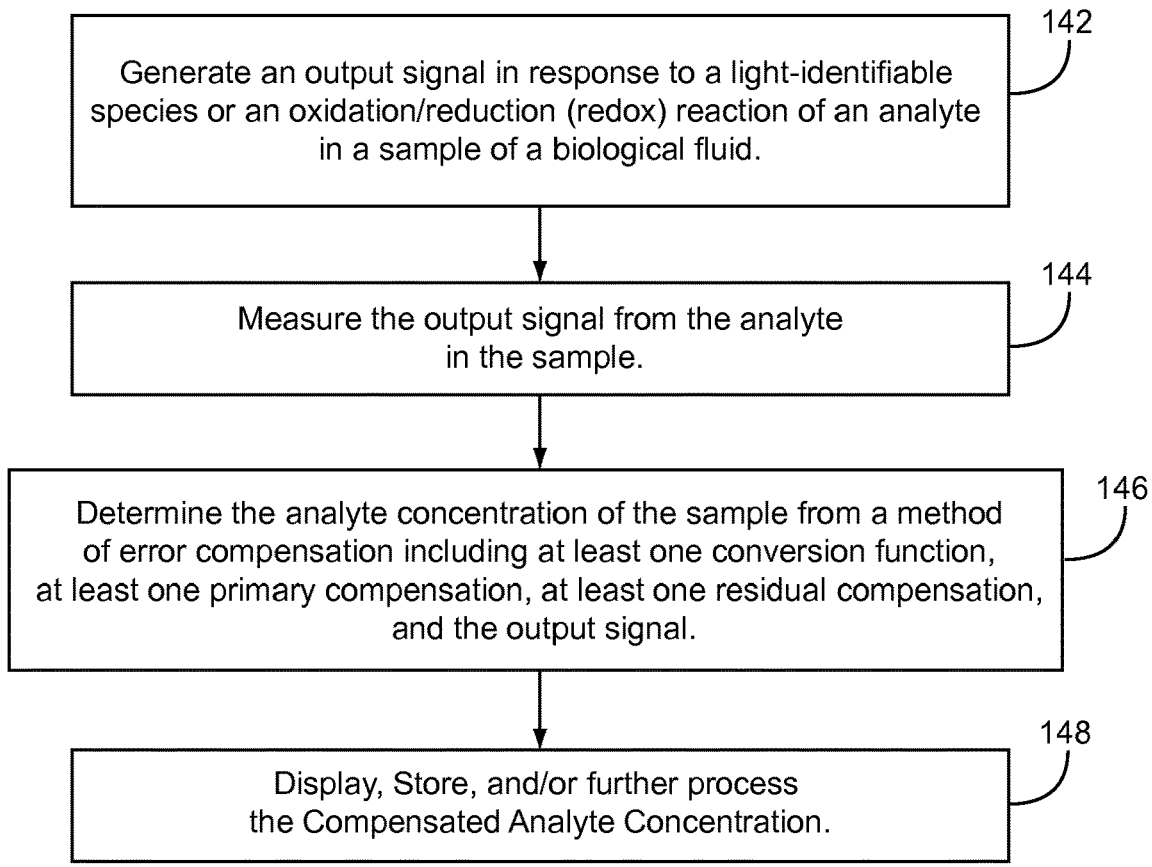
FIG. 1A represents a method for determining an analyte concentration in a sample of a biological fluid.

FIG. 1A represents a method for determining an analyte concentration in a sample of a biological fluid. In 142, the biosensor system generates an output signal in response to either a light-identifiable species or an oxidation/reduction (redox) reaction of an analyte in a sample of a biological fluid. In 144, the biosensor system measures the output signal. In 146, the analyte concentration is determined from a compensation method including at least one conversion function, at least one primary function, and at least one residual function and the output signal. In 148, the compensated analyte concentration may be displayed, stored for future reference, and/or used for additional calculations.

In 142 of FIG. 1A, the biosensor system generates an output signal in response to a light-identifiable species or an oxidation/reduction (redox) reaction of an analyte in a sample of a biological fluid. The output signal may be generated using an optical sensor system, an electrochemical sensor system, or the like.

In 144 of FIG. 1A, the biosensor system measures the output signal generated by the analyte in response to the input signal applied to the sample, such as from a redox reaction of the analyte. The system may measure the output signal continuously or intermittently. For example, the biosensor system may measure the output signal intermittently during the pulses of a gated amperometric input signal, resulting in multiple current values recorded during each pulse. The biosensor may measure the output signal from the analyte directly or indirectly through an electrochemical mediator. The biosensor system may show the output signal on a display and/or may store the output signal or portions of the output signal in a memory device.

In 146 of FIG. 1A, the analyte concentration of the sample may be determined using a method of error compensation including at least one conversion function, at least one primary compensation, at least one residual compensation, and the output signal.

Figure 1B:
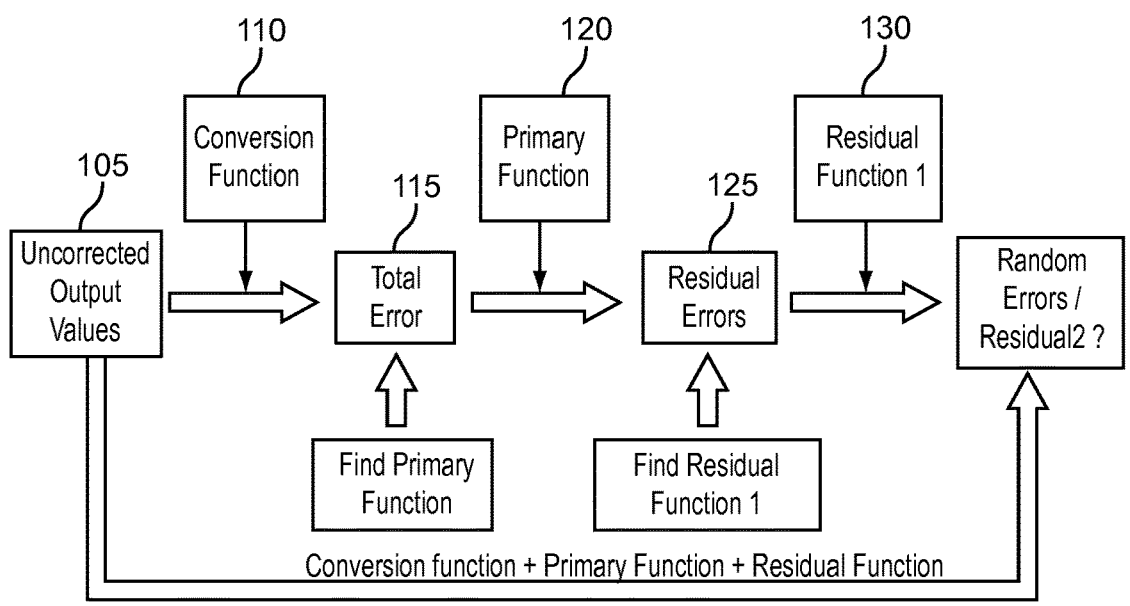
FIG. 1B represents the method of error compensation including a conversion function, primary compensation, and at least one residual compensation.

FIG. 1B represents the method of error compensation including a conversion function 110, primary compensation, and residual compensation. The output from the conversion function 110 including total error 115 is compensated with a primary compensation in the form of a primary function 120. The remaining residual errors 125 are compensated with a residual compensation in the form of at least a first residual function 130. The total error 115 includes primary and residual errors. The total error 115 also may include random and/or other types of errors. The conversion function 110, the primary function 120, and the first residual function 130, may be implemented as three separate mathematical equations, a single mathematical equation, or otherwise. For example, the conversion function 110 may be implemented as a first mathematical equation and the primary function 120 and the first residual function 130 combined and implemented as a second mathematical equation.

In FIG. 1B, uncorrected output values 105 may be output currents responsive to amperometric, voltammetric, or other input signals generating an output signal having a current component. The uncorrected output values may be output potentials responsive to potentiometry, galvanometry, or other input signals generating an output signal having a potential component. The uncorrected output values may be output signals having a current or potential component responsive to the light detected by the detector of an optical system. The output signal is responsive to a measurable species in the sample. The measurable species may be the analyte of interest or a mediator whose concentration in the sample is responsive to that of the analyte of interest.

The conversion function 110 is preferably a correlation relationship between the uncorrected output values 105 generated from a sample in response to an input signal from a measurement device and one or more reference analyte concentrations determined at known physical characteristics and environmental aspects of the sample. For example, the sample may be a whole blood sample having a known hematocrit content of 42% where the analysis is performed at a known constant temperature of 25° C. The correlation relationship between known sample analyte concentrations and uncorrected output signal values may be represented graphically, mathematically, a combination thereof, or the like. Correlation relationships may be represented by a program number (PNA) table, another look-up table, or the like that is predetermined and stored in the measurement device.

The primary function 120 providing the primary compensation may include a slope-based function, a complex index function, or other compensation function focusing on the reduction of errors, such as temperature and hematocrit, in the analysis. For example, the observed total error of a biosensor system including a measurement device and a test sensor may be expressed in terms of $\Delta S/S$ (normalized slope deviation) or $\Delta G/G$ (relative glucose errors). The primary function 120 may compensate at least 50% and preferably at least 60% of the total error 115. The analysis error remaining in the analyte concentration not compensated by the primary function may be considered to arise from operating condition, manufacturing variation, and/or random errors. Suitable primary compensation techniques may be found in Intl. Pub. No. WO 2009/108239 and Intl. Pub. No. WO 2010/

077660, for example. The conversion function 110 may be mathematically integrated with the primary function 120.

When the sample is whole blood and the analyte is glucose, the compensation provided by the primary function 120 may be substantially limited to compensation for analysis errors arising from temperature and hematocrit. Thus, by characterizing the biosensor system with respect to temperature and hematocrit change, the effects from temperature and hematocrit may be compensated by the primary function 120. Other error sources independent of temperature and hematocrit, such as the operating conditions of the system, are preferably not characterized and thus not included in the primary function 120.

Preferable primary functions are index functions that may be determined using error parameter values from the analysis of the analyte, such as the intermediate signals from the analyte responsive output signal, or from sources independent of the analyte responsive output signal, such as thermocouples, additional electrodes, and the like. Error parameters may be any value responsive to one or more errors in the output signal. Error parameter may be values from the analysis of the analyte, such as the intermediate signals from an analytic output signal, or from secondary output signals independent of the analytic output signal, such as from thermocouple currents or voltages, additional electrode currents or voltages, and the like. Thus, the error parameters may be extracted directly or indirectly from the output signal of the analysis and/or obtained independently from the analytic output signal. Other error parameters may be determined from these or other analytic or secondary output signals. Any error parameter may be used to form the term or terms that make up the index function, such as those described in Intl. Pub. No. WO 2009/108239, filed Dec. 6, 2008, entitled "Slope-Based Compensation," and the like. A more detailed treatment of error correction using index functions and slope deviation values also may be found in this publication.

An index function is responsive to at least one error parameter. An index function may be a calculated number that correlates with an error parameter, such as hematocrit or temperature, and represents the influence of this error parameter on bias. Index functions may be experimentally determined as a regression or other equation of the plot between the deviation from a reference slope and the error parameter. Thus, the index function represents the influence of the error parameter on the slope deviation, normalized slope deviation, or percent bias.

Index functions are complex when they include combinations of terms modified by weighing coefficients. The combination is preferably a linear combination, but other combination methods may be used that provide weighing coefficients for the terms. Each term may include one or more error parameters. The terms included in the complex index function may be selected with one or more exclusion tests. More preferable primary functions are complex index functions, such as those described in Intl. Pub. No. WO 2010/077660. Other primary compensation techniques may be used.

The first residual function 130 providing at least a portion of the residual compensation is applied in addition to compensating the primary errors with the primary function 120. Residual errors from error contributors other than temperature and hematocrit may be identified and correlated with one or more index functions. The difference in error between analyses performed in a controlled environment or by a HCP and user self-testing may be expressed generally by Residual Errors=total errors observed−primary function values. Thus, the residual error may be thought of as the non-random error and the manufacturing variation error minus the error projected to be compensated by the primary compensation, such as by the primary function.

The observed residual errors substantially lack the errors removed from the total error by the values of the primary function 120. The total error includes errors from substantially different sources and/or test cases, such as temperature and hematocrit error determined in a controlled environment (substantially described by the primary function), versus operating condition errors originating from outside of a controlled environment (substantially described by the residual function) and manufacturing variation. The first residual function 130 may compensate at least 5%, preferably at least 10%, and more preferably at least 20% of the total error 115. Together, the primary function 120 and the first residual function 130 may compensate at least 60%, and preferably at least 70% of the total error 115.

Residual Error also may be expressed generally by: Residual Error=(1+total error observed)/(1+primary function values)−1. In this form, the residual error is the relative error of an analyte determination after applying the primary compensation function. It therefore has the same form as the observed total error, but instead of being applied to the raw analyte (currents (nA)/Calibration Slope), it is applied to augment the primary function value. In combination, primary and residual functions may compensate for total non-random errors in the analysis.

By focusing on the residual errors in a particular situation, such as user self-testing by inexperienced subjects, and finding at least one residual function associated with the residual errors, the measurement performance of the biosensor system may be improved. Residual errors remaining after application of the first residual function 130 may be further reduced if a second residual function is applied.

While the errors described by a second residual function may be from either a controlled environment or a non-controlled environment, the errors are preferably non-random errors remaining after primary compensation and/or errors remaining after primary and first residual function compensation. For example, the second residual function may be selected to compensate errors arising at extreme temperature and/or sample hematocrit levels, such at 5° C. and 70% Hct. Thus, the second residual function may be selected to compensate for errors outside of the normal condition range of the primary or the primary and first residual functions. The second residual function also may be selected to compensate systematic deficiencies in the compensation provided by the primary or primary and first residual functions. As the residual errors also may include errors not fully compensated by the primary and first residual functions, the second residual errors may be at least partially responsive to the primary function and/or the first residual function. Thus, the second residual errors may not be responsive to the primary and/or first residual functions or the second residual errors may be at least partially responsive to the primary and/or first residual functions.

In addition to including primary compensation and at least one residual compensation, the method of error compensation represented in FIG. 1B may include the ability to adjust the compensation provided by the primary compensation in relation to the compensation provided by the residual compensation. The residual compensation also may include the ability to adjust the compensation provided by the first and second residual functions when more than one residual function is used. The error compensation provided by the primary compensation in relation to the compensation provided by the residual compensation may be adjusted because the function or functions making up the residual compensation may be taken from predetermined values stored in the measurement device as a database or otherwise for a limited temperature and/or hematocrit range, while the primary function may be determined from a full range of temperatures and hematocrits. Thus, the primary function may be determined from inputs acquired during the analysis of a sample, while a finite number of residual functions may be predetermined and stored in the measurement device. The error compensation provided by the primary compensation in relation to the compensation provided by the residual compensation also may be adjusted because some overlap may occur between the error described by the primary and one or more residual functions. There may be other reasons to adjust the error compensation provided by the primary compensation in relation to the compensation provided by the residual compensation.

One method of adjusting the error compensation provided by the primary compensation in relation to the compensation provided by the residual compensation includes weighing coefficients. Weighing coefficients may have positive or negative values or may be zero. Weighing coefficients may be determined through the statistical processing of the data collected from a combination of multiple analyte concentrations, different hematocrit levels, different temperatures, and the like.

Compensation in a general form where the error compensation provided by the primary compensation is adjusted in relation to the compensation provided by the residual compensation may be expressed as: Primary function+ WC*Residual function, where WC is the weighing coefficient. The weighing coefficient WC may be selected as a function of temperature and/or hematocrit for varying compensation contributions from the residual function. Similarly, compensation including one or more residual functions where the residual functions are each modified by a weighing coefficient may take the following general forms:

Compensated analyte concentration=current nA/(Slope$_{Cal}$*(1+primary function+WC1*residual1+ WC2*residual2 ... )), where WC1 and WC2 are weighing coefficients having values between 0 and 1 and allow the effect of the residual function to be reduced or eliminated when conditions are outside those that were used to develop the residual function. Residual1 is the first level of residual compensation after the primary compensation function, while Residual2 is the next level of residual compensation, but may not be available if an error source/index function is not found. Residual1 and Residual2 are preferably independent of each other and of the primary function.

Weighing coefficients for the primary versus residual compensation and/or for one or more residual functions may be predetermined and stored in the measurement device in the form of a table or through other means. For example, the WC1 and WC2 values may be characterized in a two-dimensional table as a function of temperature and hematocrit. In this way, the weighing coefficient table may be structured to improve the measurement performance of the biosensor system by reducing the effect of the residual function or functions on the determined analyte concentration when the hematocrit content of the sample and the temperature at which the analysis is performed are relatively close to the conditions under which the data was obtained that was used to determine the conversion function 110.

Table A, below, is an example of predetermined weighing coefficient values for multiple %-Hct values and temperatures presented in a two dimensional table.

TABLE A

| Temp ° C. | %-Hct | | | | | | |
|---|---|---|---|---|---|---|---|
| | 0 | 15 | 20 | 30 | 55 | 65 | 70 |
| 5 | 0 | 0 | 0 | 0 | 0 | 0 | 0 |
| 13 | 0 | 0 | 0 | 0 | 0 | 0 | 0 |
| 15 | 0 | 0 | 0.5 | 0.5 | 0.5 | 0.5 | 0 |
| 17 | 0 | 0 | 0.5 | 1 | 1 | 0.65 | 0.25 |
| 28 | 0 | 0 | 0.5 | 1 | 1 | 0.65 | 0.25 |
| 35 | 0 | 0 | 0.5 | 1 | 1 | 0.5 | 0 |
| 40 | 0 | 0 | 0 | 0.5 | 0.5 | 0 | 0 |
| 45 | 0 | 0 | 0 | 0 | 0 | 0 | 0 |

The values of Table A may be expanded to additional %-Hct and temperature values using linear interpolations (grading periods) between two of the fixed WC values as shown in Table B, below, for example.

TABLE B

| Temp ° C. | % Hct | | | | | | | | | | |
|---|---|---|---|---|---|---|---|---|---|---|---|
| | 0 | 15 | Grading period | 20 | Grading period | 30 | 55 | Grading period | 65 | Grading period | 70 |
| 5 | 0 | 0 | 0 | 0 | 0 | 0 | 0 | 0 | 0 | 0 | 0 |
| 13 | 0 | 0 | 0 | 0 | 0 | 0 | 0 | 0 | 0 | 0 | 0 |
| grading | 0 | 0 | | | | | | | | | 0 |
| 15 | 0 | 0 | | 0.5 | | 0.5 | 0.5 | | 0.5 | | 0 |
| grading | 0 | 0 | | 0.5 | | | | | | | |
| 17 | 0 | 0 | | 0.5 | | 1 | 1 | | 0.65 | | 0.25 |
| 28 | 0 | 0 | | 0.5 | | 1 | 1 | | 0.65 | | 0.25 |
| grading | 0 | 0 | | 0.5 | | 1 | 1 | | | | |
| 35 | 0 | 0 | | 0.5 | | 1 | 1 | | 0.5 | | 0 |
| grading | 0 | 0 | | | | | | | | | 0 |
| 40 | 0 | 0 | 0 | 0 | | 0.5 | 0.5 | | 0 | 0 | 0 |
| grading | 0 | 0 | 0 | 0 | | | | | 0 | 0 | 0 |
| 45 | 0 | 0 | 0 | 0 | 0 | 0 | 0 | 0 | 0 | 0 | 0 | or using the alternative general form of residual:

Compensated analyte concentration=current nA/(Slope$_{Cal}$*(1+primary function)*(1+WC1*residual1) *(1+WC2*residual2) ... ), Table A and Table B demonstrate that the weighing coefficients in the area from 30 to 55%-Hct and from 17 to 28° C. are 1, meaning a full contribution from the residual function is provided to the compensation method. However, the weighing coefficient for 30%-Hct at 16° C., for example, is a linear interpolation value of the two values at 15 and 17° C., which is 0.75 ((0.5+1)/2). Similarly, the value at 25% Hct and 20° C. is a linear interpolation of the values at 20 and 30%-Hct, which is 0.75 ((0.5+1)/2). Temperature may be taken or estimated from any means, including from a thermocouple in the measurement device or from the sample. %-Hct may be calculated or estimated from an equation, a Hct sensing electrode, a combination of these, or from other means.

Figure 1C:
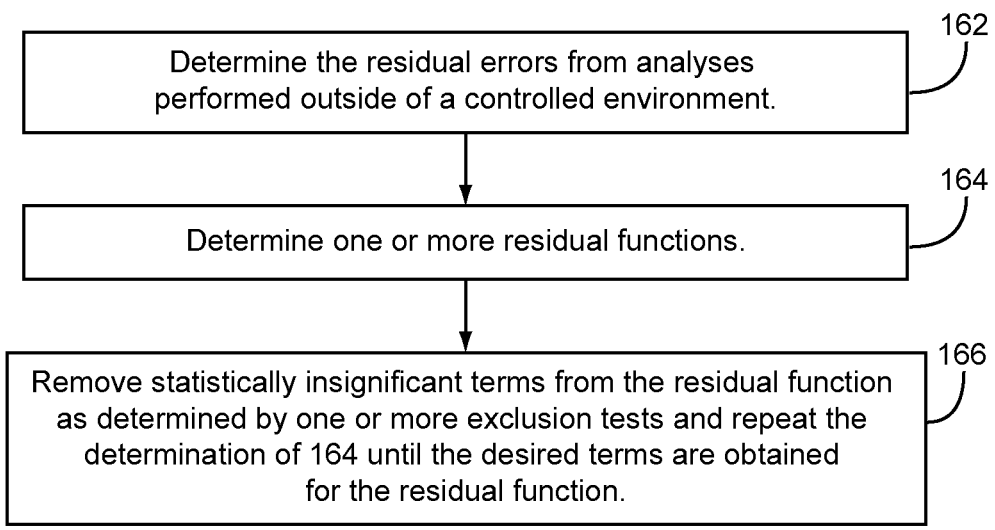
FIG. 1C represents a general method for determining a residual function or functions responsive to a non-controlled environment test case, such as for user self-testing.

FIG. 1C represents a general method for determining a residual function or functions responsive to a non-controlled environment test case, such as for user self-testing.

In 162, determine the residual errors from analyses performed outside of a controlled environment, such as by user self-testing. This determination may be made through the following relationship:

Residual errors=total errors−primary function values where, total errors are present in data collected from analyses performed outside of the controlled environment and may be collected from self-testing, HCP-testing, and/or any other testing introducing error from the testing process that is substantially absent from controlled environment testing.

In 164, determine one or more residual functions. This determination may be made by performing a multi-variable regression using the observed residual errors as the responder and various terms from internal and external signals as the predictors. Other mathematical techniques may be used to determine the one or more residual functions.

In 166, remove statistically insignificant terms from the residual function as determined by one or more exclusion tests, such as with p-value thresholds or T-values, and repeat the determination 164 until the desired terms are obtained for the residual function.

Figure 1D:
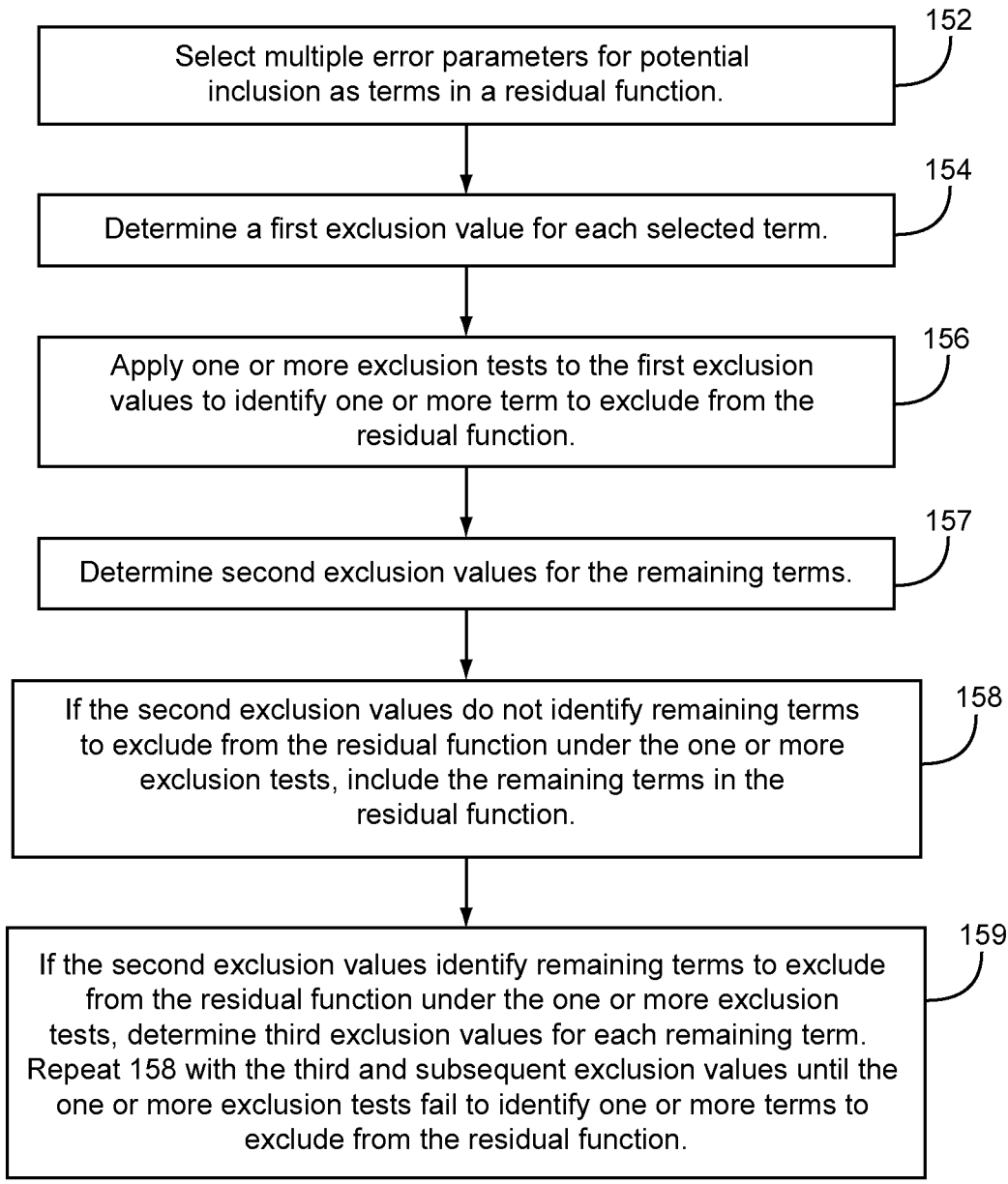
FIG. 1D represents a method for selecting terms for inclusion in a residual function.

FIG. 1D represents an iterative method for selecting terms for inclusion in a residual function. In 152, multiple error parameters are selected as terms for potential inclusion in the residual function. The error parameters may be extracted directly or indirectly from an output signal responsive to a light-identifiable species or from the redox reaction of an analyte in a sample of a biological fluid. The error parameters also may be obtained independently from the output signal, such as from the output signal of a thermocouple or other device. The terms may include values other than error parameters, such as uncompensated analyte concentration values and the like. Preferably, the selected terms exclude terms and/or error parameters selected for total or substantial compensation by the primary function. More preferably, the selected terms exclude terms eliminated through one or more exclusion tests. In this manner, the errors compensated by the residual function may be different than the errors compensated by the primary function. Also, as an error in the determined analyte concentration can be described in different ways by two or more different error parameters or terms, through term selection a residual function can compensate for error left over from the primary function, while doing so in a different way through the use of one or more terms not included in the primary function. Thus, residual functions preferably include different terms than those in the primary function.

In 154, one or more mathematical techniques are used to determine first exclusion values for each selected term. The mathematical techniques may include regression, multi-variant regression, and the like. The exclusion values may be p-values, T-values, or the like. The mathematical techniques also may provide weighing coefficients, constants, and other values relating to the selected terms.

In 156, one or more exclusion tests are applied to the exclusion values to identify one or more terms to exclude from the residual function. At least one term is excluded under the test. In 157, the one or more mathematical techniques are repeated to identify second exclusion values for the remaining terms. In 158, if the second exclusion values do not identify remaining terms for exclusion from the residual function under the one or more exclusion tests, the remaining terms are included in the residual function. In 159, if the second exclusion values identify remaining terms to exclude from the residual function under the one or more exclusion tests, the one or more mathematical techniques of 157 may be repeated to identify third exclusion values for the remaining terms. These remaining terms may be included in the residual function as in 158 or the process may be iteratively repeated as in 159 until the exclusion test fails to identify one or more terms to exclude.

p-values may be used as exclusion values for an exclusion test to select terms for potential exclusion from the residual function. p-values indicate the probability of a term affecting the correlation between the residual function and the residual errors if the term were eliminated from the residual function. Thus, the exclusion test may eliminate terms having a p-value higher than an exclusion value threshold. For example, when the exclusion test uses p-values as exclusion values, exclusion p-values from about 0.01 to about 0.10 are preferred, with exclusion p-values from about 0.03 to about 0.07 being more preferred. The smaller the numerical p-value selected as an exclusion threshold value, the more terms will be excluded from the residual function.

When the undesired terms have been excluded under a first exclusion test, such as with p-values, additional terms may be excluded using a second exclusion test, such as with T-values. For example, if the terms remaining after multiple p-value exclusion tests have zero or near zero p-values, thus failing further exclusion under the p-value exclusion test, the T-values of the terms remaining may be used to exclude terms under a T-value threshold. In addition to exclusion tests based on p-values and T-values, other exclusion tests also may be used to identify potential terms for exclusion from the residual functions.

Removing undesired terms from the residual function that do not substantially affect the correlation between the residual function and the residual errors allows for the desired correlation between the residual function and the residual errors to be determined. Preferably, an iterative process of selecting and eliminating terms with the largest undesirable departure from an exclusion test is repeated until the remaining terms meet the test. Thus, the desired improvement in measurement performance may be achieved by the compensation method having a simplified function, while providing a shorter analysis time. Furthermore, the precision of subsequent analyses performed using different biosensor systems and conditions may be improved through the removal of undesirable terms from the residual function.

Table 1, below, lists the terms (predictors), weighing coefficients, p-values, and T-values resulting from a multi-variable regression of data taken from glucose output signals (currents) from multiple clinical studies using test sensors from multiple test sensor lots. Approximately 100 to 134 glucose concentrations were determined (approximately 2 measurements per sensor lot for each blood sample). The samples were analyzed using a gated amperometric input signal where selected intermediate output signals were recorded from the pulses. Temp represents temperature and $G_{raw}$ is the determined analyte concentration of the sample without compensation. The ratio parameter, R3/2, represents the relationship between the last currents generated by the analyte in response to the $3^{rd}$ and $2^{nd}$ pulses of a gated amperometry pulse sequence including 6 pulses. Similarly, R32G represents a product from R3/2 and $G_{raw}$, while TR32 represents a product from temperature and R3/2, for example.

MINITAB version 14 software was used with the Multi-Variant Regression of Linear Combinations of Multiple Variables option chosen to perform the multi-variable regression. Other statistical package software or regression options may be used to determine the weighing coefficients for the terms. With regard to Table 1, below, a p-value exclusion threshold of 0.05 was used to exclude all terms having a p-value higher than 0.05. The first multivariable regression identified terms TR43 and TR53 for removal from the residual function. Repeating the regression yielded the values in Table 1.

TABLE 1

| Terms | Weighing Coefficient | Coefficient Standard Error | T-value | p-value |
|---|---|---|---|---|
| Constant | −0.1493 | 0.2473 | −0.60 | 0.546 |
| Temp | −0.11042 | 0.02763 | −4.00 | 0.000 |
| $G_{raw}$ | 0.104235 | 0.006584 | 15.83 | 0.000 |
| R3/2 | 0.149998 | 0.008681 | 17.28 | 0.000 |
| R4/3 | −0.9442 | 0.2651 | −3.56 | 0.000 |
| R5/4 | −4.7200 | 0.3204 | −14.73 | 0.000 |
| R5/3 | 0.7120 | 0.2274 | 3.13 | 0.002 |
| R6/5 | 5.1886 | 0.2028 | 25.58 | 0.000 |
| R32G | −0.00117486 | 0.00006767 | −17.36 | 0.000 |
| R43G | 0.016249 | 0.003656 | 4.44 | 0.000 |
| R54G | −0.105871 | 0.006976 | −15.18 | 0.000 |
| R53G | −0.015966 | 0.003684 | −4.33 | 0.000 |
| R65G | −0.125305 | 0.009622 | −13.02 | 0.000 |
| R64G | 0.128145 | 0.009871 | 12.98 | 0.000 |
| TR32 | −0.0052691 | 0.0003922 | −13.43 | 0.000 |
| TR54 | 0.39391 | 0.03143 | 12.53 | 0.000 |
| TR65 | −0.09364 | 0.02756 | −3.40 | 0.001 |
| TR64 | −0.19516 | 0.02922 | −6.68 | 0.000 |

S = 0.0378990
R-Sq = 38.9%
R-Sq(adj) = 38.7%

A final compensation function may then be generally determined for the analysis as follows:

Final compensation function=primary function+ WC*residual function where, a primary function is combined with the determined residual function optionally modified with a weighing coefficient.

Conventional compensation methods/algorithms derived from controlled environment testing data have the disadvantage of being unable to compensate the self-testing data from users without decreasing measurement performance with regard to HCP-testing data. Traditionally, the mean percent bias of self-testing data is 3% to 4% higher than controlled environment testing and HCP-testing data. Thus, while self-testing errors could be at least partially compensated by introducing a mean percent bias offset of −3% to −4% for analyses performed under a self-testing test case, the determined analyte concentrations on average would be approximately 3 to 4% too low if this offset were applied to controlled environment or HCP test cases.

Figure 2A:
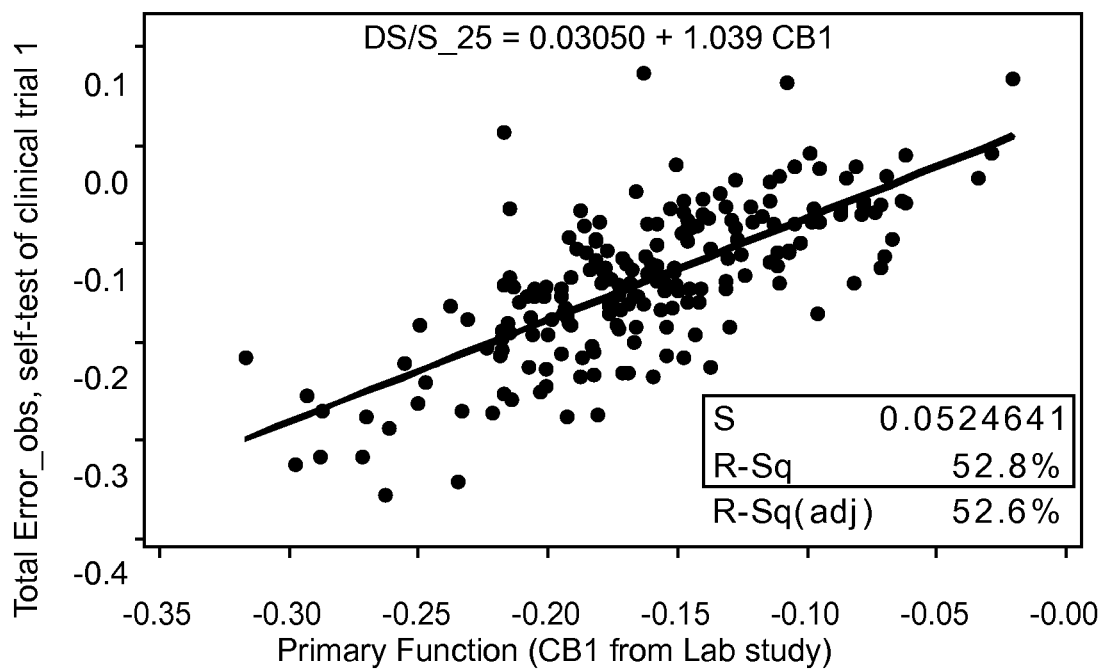
FIG. 2A is the correlation plot between the total errors from self-testing of two sensor lots in a clinical trial and the primary function.
Figure 2B:
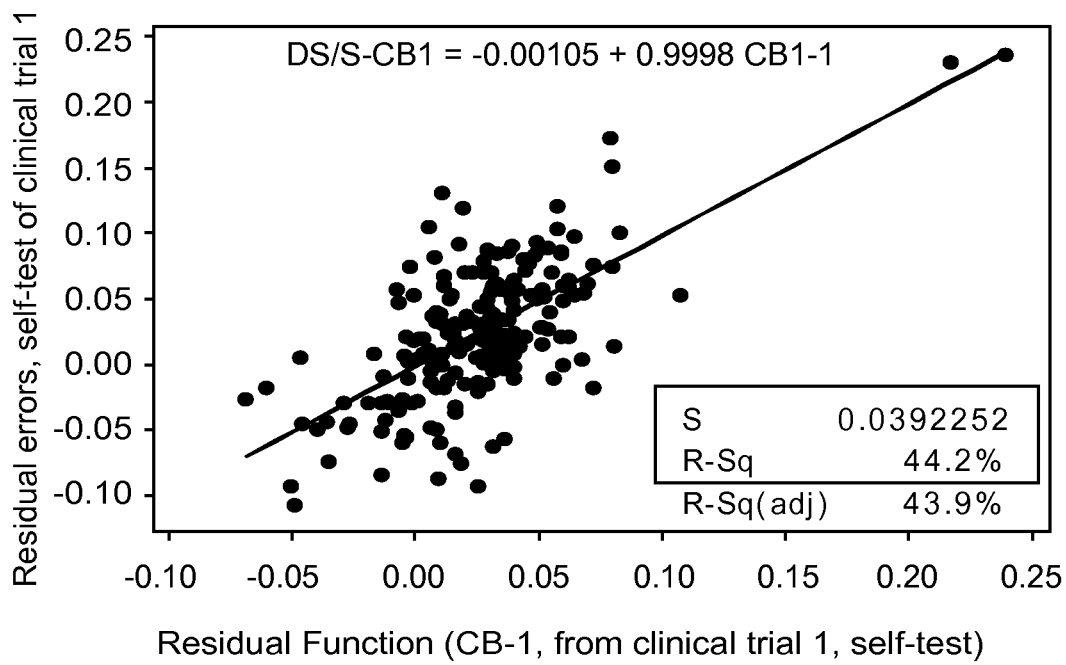
FIG. 2B is the correlation plot between the observed residual errors from self-testing and the residual function values after extraction of the residual function.
Figure 2C:
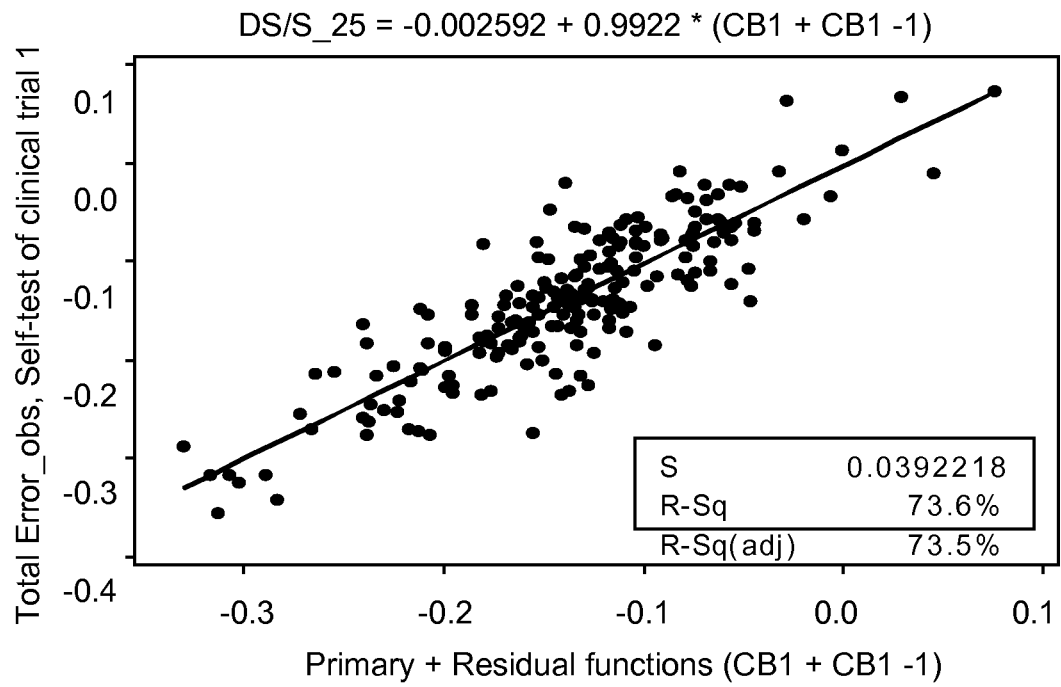
FIG. 2C is the correlation plot between the total errors from self-testing of two test sensor lots in a clinical trial and the sum of primary and residual function values.

FIG. 2A, FIG. 2B, and FIG. 2C show the progression of residual function extraction from the glucose concentrations determined by multiple users with a biosensor system. The users self-tested with a measurement device that applied a gated amperometric input signal having five excitations to the test sensors, and the test sensors were from two different manufacturing lots.

FIG. 2A is the correlation plot between a primary function (primary function designated CB1 in the figure) and the total errors present in the determined glucose concentrations. FIG. 2A shows a correlation slope that is about 4% higher than the expected value of 1.00 and a correlation intercept that is about 3% higher than the expected value of zero. The overall correlation coefficient is 52.8% for the primary function values in predicting the total error. FIG. 2B is the correlation plot between the residual errors in the determined glucose concentrations and residual function values after extraction of the residual function as previously described (residual function designated CB1-1 in the figure). FIG. 2C is the correlation plot between the total errors present in the determined glucose concentrations and the sum of primary and residual function values (designated CB1+CB1-1). The residual function provided improvement in that the correlation slope and intercept were brought closer to their expected values of 1 and 0. The combination of the primary function with the residual function provided an increase of about 0.2 in the correlation coefficient for the data and the Syx value (the standard deviation of the total error) was reduced from 0.0524 to 0.0392, a 25% improvement ([0.0524−0.0392]/0.0524*100).

FIG. 2A shows that primary compensation described about 53% of the total error, while FIG. 2B shows that residual compensation described about 44% of the remaining 47% error, or about 20% of the total error. FIG. 2C shows that in combination, primary and residual compensation described about 74% of the error. Thus, a significant increase in the measurement performance of the biosensor system for self-testing analyses was observed as the residual function increased the ability of the compensation method to describe the total error. Thus, a compensation method including a primary function and at least one residual function describes at least 60%, preferably at least 70%, of the total error from at least 40, preferably from at least 80, and more preferably from at least 100 user self-testing analyses.

Table 2, below, provides the error compensation results from two self-testing test cases. Clinical trial 1 included about 52 participating subjects who self-tested twice and also were tested twice by an HCP using test sensors from two lots (A and B) to provide at total of about 400 analyses. Clinical trial 2 also included about 52 subjects who self-tested twice and also were tested twice by an HCP using test sensors from two lots (A and B) to provide an additional about 400 analyses. The data set from clinical trial 1 was used to determine the residual functions (thus as "training data") in conjunction with the pre-determined primary function from lab data, while the data from clinical trial 2 provided the results from the compensated analyses. The following abbreviations are used in the table:

Un-comp: initial glucose sample concentration estimate from conversion function using a correlation between output current and glucose concentration, thus lacking any compensation for physical, environmental, operating condition, or manufacturing variation errors.

CB1: a primary function extracted from the data obtained in a controlled environment from whole blood samples having glucose concentrations of 75, 150, 300 or 400 mg/dL, hematocrit levels of 20%, 40% or 70%, and target analysis temperatures of 15, 22, or 30° C. The primary error compensation was designed to capture the major effects of temperature and hematocrit.

CB1-1: residual function extracted from the self-testing data set of Clinical trial 1.

CB1-2: residual function extracted from the HCP and self-testing data sets of Clinical trial 1.

The results are reported in Table 2, below, as follows:

(1) CB1 column: compensated by the primary function CB1 only.

(2) CB1-1 column: compensated by CB1+CB1-1 residual function.

(3) CB1-2 column: compensated by CB1+CB1-2 residual function.

TABLE 2

|  |  | Clinical trial 1, 5-excitation input signal (Training data set) | | | | Clinical trial 2, 5-excitation input signal (Testing data set) | | | |
| --- | --- | --- | --- | --- | --- | --- | --- | --- | --- |
|  |  | Un-comp | CB1 | CB1-1 | CB1-2 | Un-comp | CB1 | CB1-1 | CB1-2 |
| Lot A, HCP | Mean Percent bias | −1.56 | 1.150 | −1.000 | −0.280 | −3.57 | 2.062 | 0.250 | 1.041 |
|  | SD of Percent biases | 6.54 | 3.354 | 2.988 | 2.929 | 7.52 | 3.639 | 3.252 | 3.164 |
|  | % within ±10% | 87.3 | 99.0 | 100.0 | 99.0 | 76.9 | 97.1 | 100.0 | 100.0 |
|  | % within ±5% | 61 | 83 | 94 | 92 | 45 | 80 | 89 | 88 |
| Lot A, self-test | Mean Percent bias | 2.30 | 3.008 | 0.706 | 1.217 | 0.75 | 4.284 | 2.222 | 2.751 |
|  | SD of Percent biases | 8.62 | 6.142 | 4.833 | 5.031 | 10.67 | 6.236 | 5.958 | 5.800 |
|  | % within ±10% | 77.5 | 88.2 | 95.1 | 94.1 | 70.9 | 84.3 | 96.1 | 94.1 |
|  | % within ±5% | 48 | 55 | 70 | 69 | 36 | 49 | 68 | 67 |

For the testing data set from Clinical trial 2, the primary function reduced the percent bias standard deviation value of test sensors from Lot A under the HCP test case from 7.52 to 3.64, a reduction of close to 4 SD units, giving a measurement performance of 97.1% within a ±10% percent bias limit. The residual function (CB1-1) further reduced the percent bias standard deviation value to 3.252, thus bringing the measurement performance to 100% of the analyses within the ±10% limit. For the test sensors from Lot A under the self-testing test case, the primary function reduced the percent bias standard deviation value from 10.67 to 6.236. The residual function further reduced the percent bias standard deviation value to 5.958 from 6.236 for the primary function alone and reduced the mean percent bias from 4.284 to 2.222. This residual function (CB1-1) increased the measurement performance of the biosensor system from 84.3% to 96.1% of the analysis within the ±10% percent bias limit, thus an about 14% (96.1−84.3/84.3*100) improvement in relation to the primary function alone. Thus, a compensation method including a primary function and at least one residual function brings at least 85%, preferably at least 90%, and more preferably at least 95% of the analyte concentrations determined from at least 40, preferably from at least 80, and more preferably from at least 100 user self-testing analysis within a ±10% percent bias limit.

Figure 3A:
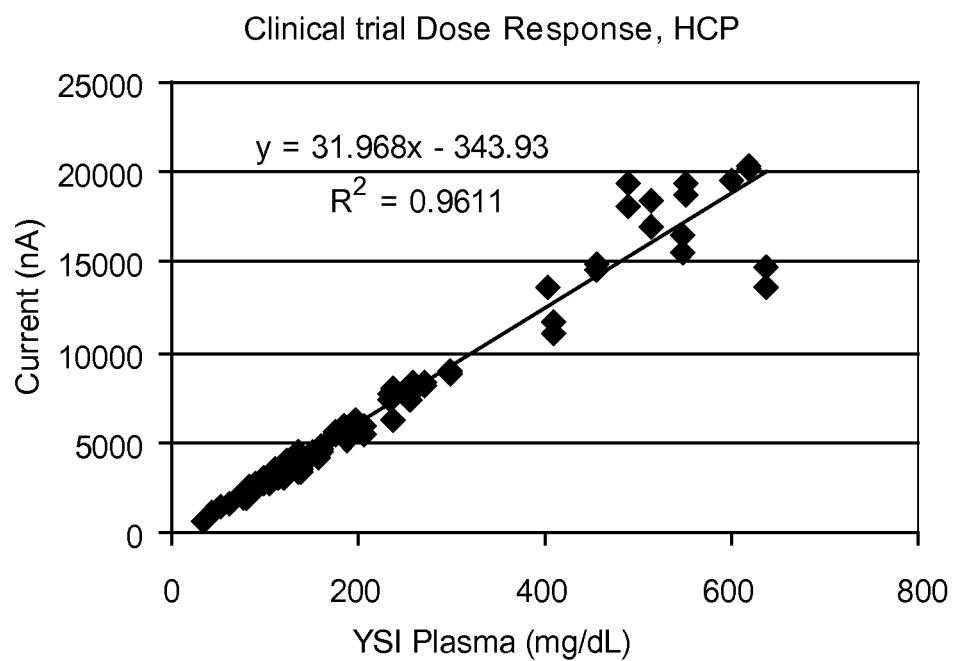
FIG. 3A is the dose response correlation plot between the output signal currents from a whole blood sample and the reference glucose concentration of each sample as determined by a YSI reference instrument.
Figure 3B:
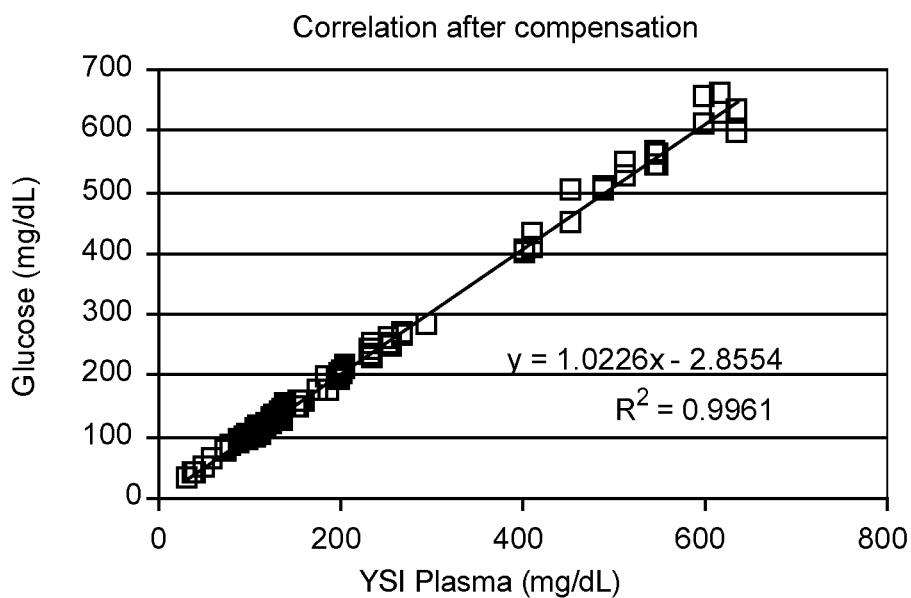
FIG. 3B shows the correlation plot after compensation of the data in FIG. 3A using error compensation including a primary function and a residual function.
Figure 3C:
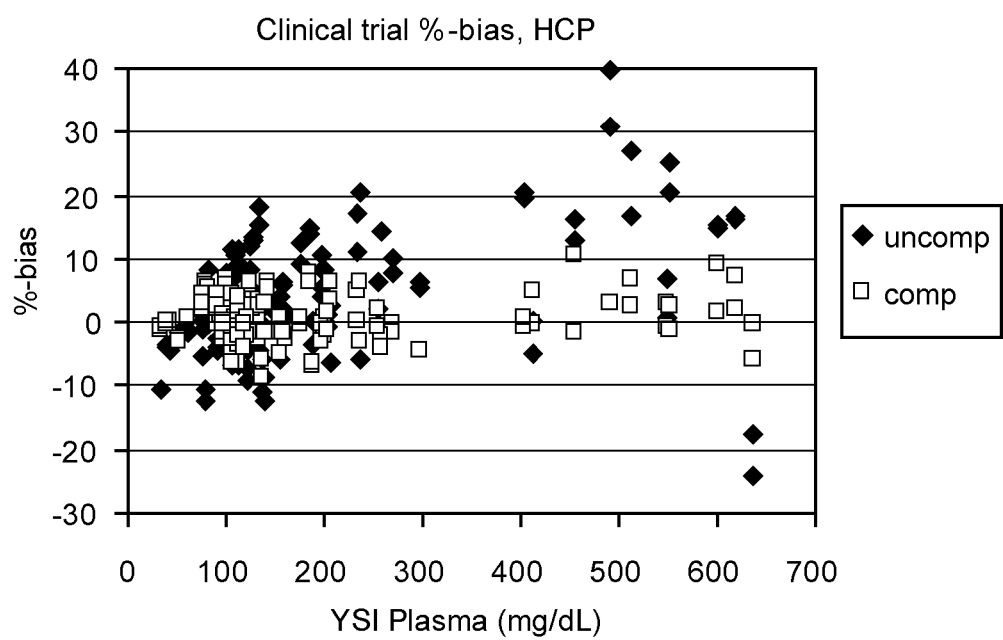
FIG. 3C plots the percent biases before and after compensation in FIG. 3A and FIG. 3B for the blood samples collected from a HCP test case, where 99.3% of the compensated data population is within ±10%.
Figure 3D:
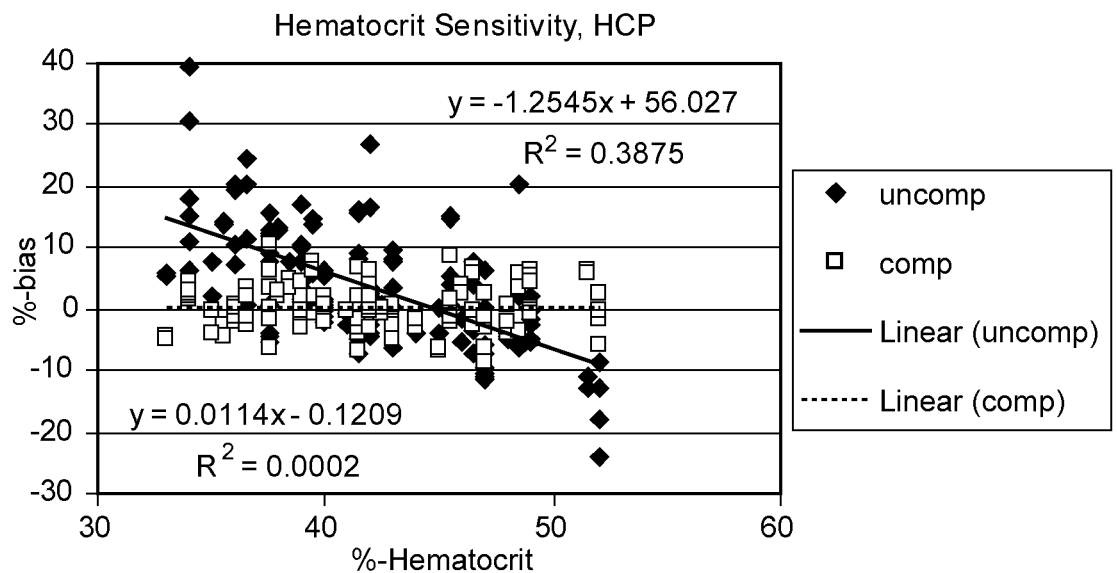
FIG. 3D shows the hematocrit sensitivity before and after compensation of the data from FIG. 3A where the hematocrit dependence of percent biases is substantially removed after compensation.

FIG. 3A through FIG. 3D depict the results obtained when error compensation using a primary and a residual function was applied to data from a HCP test-case clinical trial including approximately 134 data points (2 measurements from 67 whole blood samples). FIG. 3A is the uncompensated dose response correlation plot between the output signal currents from a whole blood sample and the reference glucose concentration of each sample as determined by a YSI reference instrument. The data demonstrated relatively large diversions from the reference concentration attributable to hematocrit as a physical error contributor and to the operating condition error contributors arising from HCP-testing. FIG. 3B shows the correlation plot after compensation of the data in FIG. 3A using error compensation including a primary function and a residual function. FIG. 3C plots the percent biases before and after compensation in FIG. 3A and FIG. 3B for the blood samples collected from a HCP test case, where 99.3% of the compensated data population is within ±10%. FIG. 3D shows the hematocrit sensitivity before and after compensation of the data from FIG. 3A where the hematocrit dependence of percent biases is substantially removed after compensation.

Table 3, below, summarizes the measurement performance of the biosensor system before and after compensation in terms of mean percent biases, percent bias standard deviation (SD), and the percentage of the determined analyte concentrations within ±5%, ±8%, and ±10% percent bias limits of the reference analyte concentration for the HCP and self-testing determined analyte concentrations. These data show that the SD values after compensation with a primary and a residual function are more than 50% reduced in relation to the uncompensated analyte determinations.

TABLE 3

|  | Mean Percent Bias | | Percent Bias SD | | Un-comp | Percent within Percent Bias Limit | | |
| --- | --- | --- | --- | --- | --- | --- | --- | --- |
|  | Un-comp | comp | Un-comp | comp | ±10% | ±10% | ±5% | ±8% |
| HCP | 3.43 | 0.36 | 9.6 | 3.52 | 70.9 | 99.3 | 82.8 | 97.8 |
| Self | 5.83 | −0.03 | 9.2 | 3.39 | 70.9 | 100.0 | 88.1 | 98.5 |

The use of primary and residual functions in combination placed about 99% of the analysis within a ±10% percent bias limit, greater than 95% of the analysis within a ±8% percent bias limit, and greater than 80% of the analysis within a ±5% percent bias limit. These results show an approximately 40%

(100%*[99.3−70.9]/70.9) improvement in relation to the uncompensated analyses at the ±10% percent bias limit. Thus, a compensation method including a primary function and at least one residual function may bring greater than 95% of determined analyte concentrations within a ±8% percent bias limit, and greater than 60%, preferably greater than 70%, and more preferably greater than 80% of the determined analyte concentrations within a ±5% percent bias limit for at least 40, preferably for at least 80, and more preferably for at least 100 user self-testing analyses.

FIG. 4A through FIG. 4D depict the results obtained when error compensation including primary and a residual functions was applied to capillary blood samples and capillary blood samples spiked with venous blood to adjust the hematocrit content of the samples. The natural hematocrit level of the capillary samples ranged from about 30% to about 53%, while the hematocrit level of the spiked venous blood samples was adjusted to range from about 20% to about 65%. The capillary blood samples spiked with venous blood also were adjusted to include from 40 to 490 mg/dL of glucose as an analyte. Thus, the spiked samples were adjusted to have hematocrit and glucose levels both above and below those normally observed in patients.

Figure 4A:
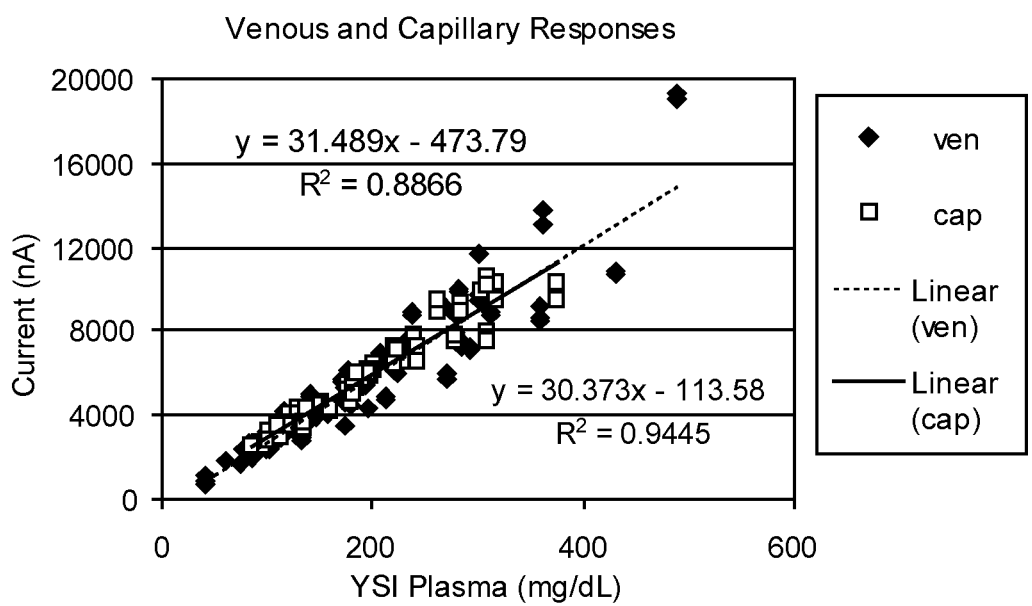
FIG. 4A is the response correlation plot between the output signal currents from the capillary and venous samples and the reference glucose concentration of each sample as determined by a YSI reference instrument.
Figure 4B:
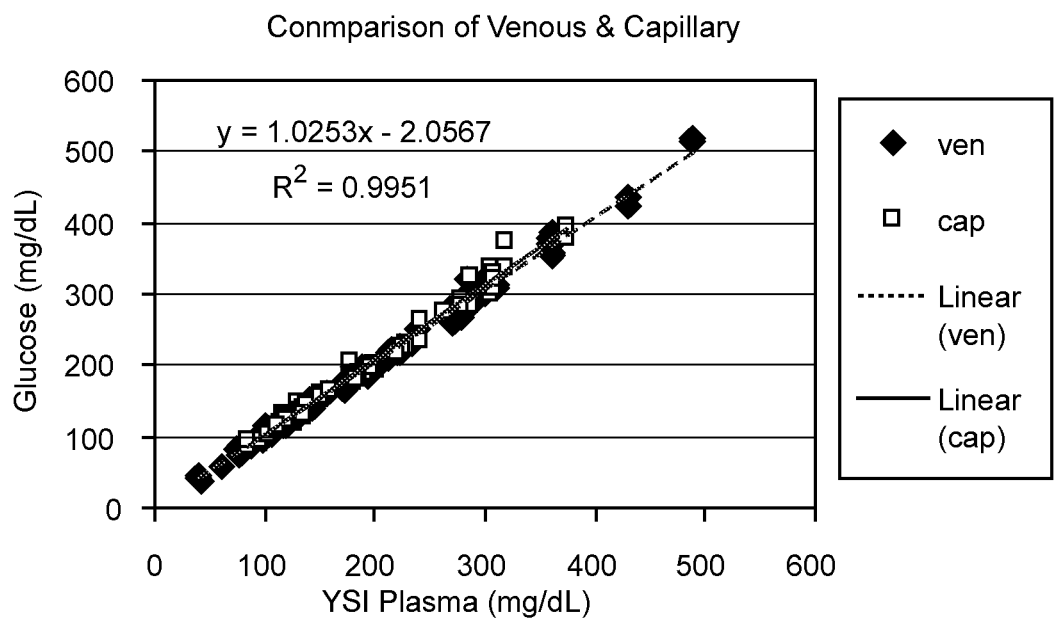
FIG. 4B shows the correlation plot after compensation of the data in FIG. 4A using the same error compensation including a primary function and a residual function for both the capillary and venous samples.

FIG. 4A is the response correlation plot between the output signal currents from the capillary and venous samples and the reference glucose concentration of each sample as determined by a YSI reference instrument. The data demonstrated relatively large diversions from the reference concentration attributable to the wide hematocrit range as a physical error contributor. FIG. 4B shows the correlation plot after compensation of the data in FIG. 4A using the same error compensation including a primary function and a residual function for both the capillary and venous samples. This plot establishes that the performances for testing capillary and venous blood samples with compensation are substantially identical.

Figure 4C:
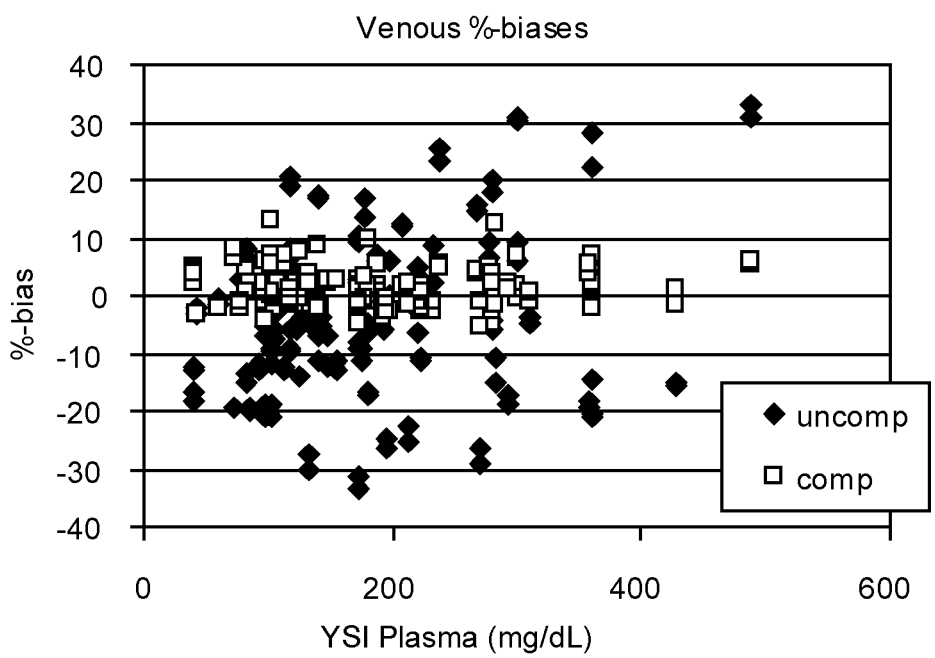
FIG. 4C plots the percent biases before and after compensation for the venous blood samples from FIG. 4A.
Figure 4D:
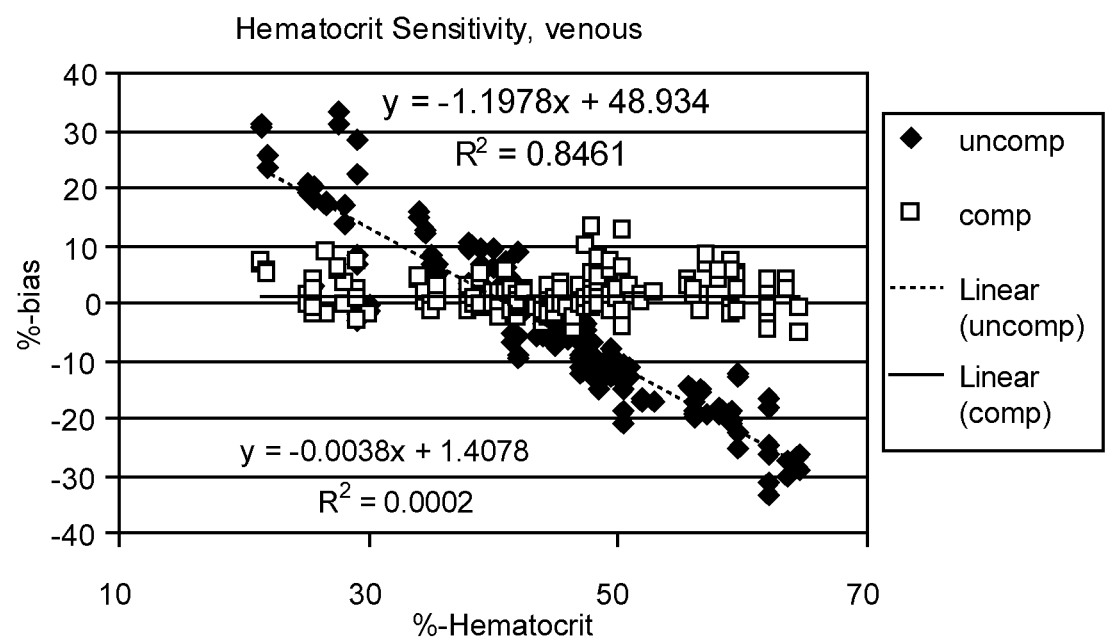
FIG. 4D shows the hematocrit sensitivity before and after compensation for the spiked venous samples where the hematocrit dependence of the percent biases is essentially removed to provide a substantially straight line after compensation.

FIG. 4C plots the percent biases in the determined analyte concentrations of the venous blood adjusted samples before and after compensation, where 98.7% of the data population is within a ±10% percent bias limit. This shows a reduction in hematocrit sensitivity, and thus an improvement in measurement performance of about 97% (100*[98.7−50]/50), as only about 50% of the un-compensated data population fell within the ±10% percent bias limit. FIG. 4D shows the hematocrit sensitivity before and after compensation for the spiked venous samples where the hematocrit dependence of the percent biases is essentially removed by the compensation to provide a substantially straight line. Before compensation, the correlation plot having a slope of about −1.2 indicates that the shows that for each 1% change in hematocrit sample content from the reference sample content, there is an approximately 1% percent bias increase present in the determined analyte concentration. Thus, a compensation method including a primary function and at least one residual function may reduce the slope of a correlation plot representing hematocrit sensitivity for whole blood samples to ±0.4 or less, preferably to ±0.2 or less, and more preferably to ±0.1 or less, when the whole blood samples include from about 30% to about 55% hematocrit, preferably from about 20% to about 70% hematocrit.

Biosensor test sensors vary from lot-to-lot in their ability to reproducibly produce the same output signal in response the same input signal and sample analyte concentration. While preferable to equip the measurement device with a single calibration curve for the conversion function, doing so limits the manufacturing variance that can occur between different lots of test sensors. A method of error compensation including primary and at least one residual function may allow for increased measurement performance being obtained from multiple test sensor lots using the same method of error compensation. Additionally, the method of error compensation including primary and at least one residual function may allow for greater lot-to-lot manufacturing variability of the test sensors while providing the desired measurement performance to the biosensor system.

Figure 5A:
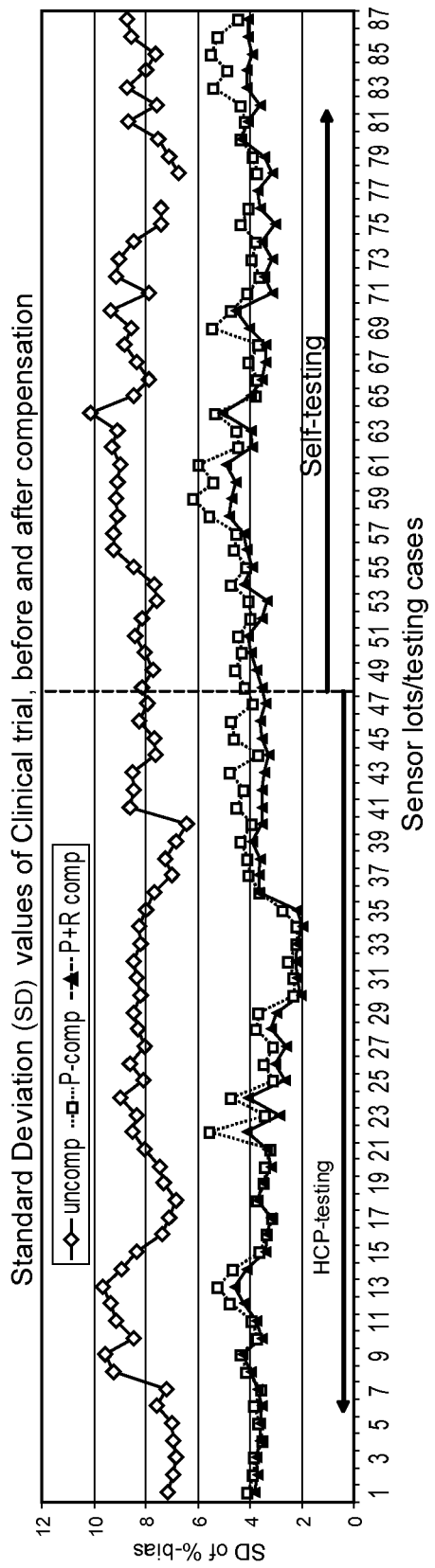
FIG. 5A shows the standard deviation of values for each test sensor lot before and after compensation for a total of 87 test cases.

FIG. 5A through FIG. 5D show the results provided by primary and the combination of primary and residual functions when approximately 10,000 test sensors were used to perform glucose concentration determinations of whole blood samples. FIG. 5A shows the standard deviation of percent bias values for each test sensor lot before and after compensation for a total of 87 test cases. In FIG. 5A, each number on the X-axis represents a subset of a different lot of test sensors with each subset including about 100 to about 130 test sensors. About 7 different lots of test sensors were used to determine glucose concentrations for venous blood under a controlled environment test case. About 40 different lots of test sensors were used to determine glucose concentrations under a HCP test case. About 40 different lots of test sensors were used to determine glucose concentrations under a user self-testing test case. The Y-axis shows the percent bias standard deviation for the multiple concentration determinations performed with each lot of test sensors.

For the HCP test case, the uncompensated analyses showed an average percent bias standard deviation of about 7.9 for the about 40 different lots of test sensors. This value was reduced to about 3.97 after compensation with a primary function. The addition of a residual function to the primary compensation provided an average percent bias standard deviation of about 3.59. For the user self-testing test case, the uncompensated analyses showed an average percent bias standard deviation of about 8.26 for the about 40 different lots of test sensors. This value was reduced to about 4.46 after compensation with a primary function. The addition of a residual function to the primary compensation provided an average percent bias standard deviation of about 3.91. The improvement in measurement performance obtained from the addition of the residual function to the primary function was most evident from the reduction in the mean percent bias from 4.17 to 0.20 for the user self-testing test case, an approximately 96% reduction (100*[4.17−0.20]/4.17). These measurement performance results are summarized in Table 4, below.

TABLE 4

| | Percent within Percent Bias Limit of ±10% | | | Mean Percent Bias | | | Percent Bias Standard Deviation | | |
|---|---|---|---|---|---|---|---|---|---|
| | Un-comp | P comp | P + R comp | Un-comp | P comp | P + R comp | Un-comp | P comp | P + R comp |
| HCP-Avg | 78.3 | 96.2 | 98.3 | 1.58 | 1.78 | −1.35 | 7.92 | 3.94 | 3.56 |
| HCP-SD | | | | 2.50 | 2.08 | 1.59 | | | |
| Self-Avg | 66.9 | 88.8 | 98.0 | 5.96 | 4.17 | 0.20 | 8.35 | 4.47 | 3.88 |
| Self-SD | | | | 2.38 | 2.06 | 1.48 | | | |
| Self-HCP | −11.4 | −7.4 | −0.3 | 4.38 | 2.39 | 1.55 | 0.45 | 0.54 | 0.32 | where HCP-Avg denotes the arithmetic average values from the HCP test cases under each indicator of measurement performance, while HCP-SD denotes the standard deviation of the average mean percent bias values; Self-Avg denotes the arithmetic average values from the user self-testing test cases under each indicator of measurement performance, while Self-SD denotes the standard deviation of the average mean percent bias values; and Self-HCP denotes the difference between the average values from HCP and user self-testing test cases.

Thus, the measurement performance results of Table 4 established that a compensation method including a primary function and at least one residual function may provide average percent bias standard deviation values of less than 5, preferably less than 4, for 5,000 or less analyses, preferably for 10,000 or less analyses, under both HCP and user self-testing test cases. The compensation method including a primary function and at least one residual function also may provide average percent bias standard deviation values of less than 5, preferably less than 4, for glucose analyses performed with test sensors from 45 or less test sensor lots, preferably from 87 or less test sensor lots, under both HCP and user self-testing test cases.

The residual function provided an about 9% (3.94–3.56/3.94*100) improvement in the average percent bias standard deviation for the HCP test case in relation to the primary function alone. The residual function also provided an about 13% (4.47–3.88/4.47*100) improvement in the average percent bias standard deviation for the self-testing test case in relation to the primary function alone. An improvement in the mean percent bias standard deviation of about 23% (2.08–1.59/2.08*100) was also provided by the residual function in relation to the primary function alone for the HCP test case. Hence, a precision improvement for substantially non-manufacturing variation errors was observed for multiple test sensor lots when a method of error compensation including a primary function and at least one residual function was used to determine the glucose concentration of whole blood samples.

The measurement performance results of Table 4 also established that a compensation method including primary and at least one residual function may provide an improvement in the number of the approximately 10,000 analyses falling within the ±10% percent bias limit. This effect was more pronounced for the user self-testing test cases where an improvement of approximately 10% (98–88.8/88.8*100) was observed when the residual function was combined with the primary function to compensate the analyses for the approximately 4200 user self-testing analyses. Thus, a compensation method including a primary function and at least one residual function may bring greater than 90%, preferably greater than 95%, of the analyte concentrations determined with 5,000 or less test sensors, preferably with 10,000 or less test sensors within a ±10% percent bias limit, under both HCP and user self-testing test cases. The compensation method including a primary function and at least one residual function also may bring greater than 90%, preferably greater than 95%, of the analyte concentrations determined from 45 or less test sensor lots, preferably from 87 or less test sensor lots, within a ±10% percent bias limit, under both HCP and user self-testing test cases. Hence, an accuracy improvement was observed for multiple test sensor lots when a method of error compensation including a primary function and at least one residual function was used to determine the glucose concentration of whole blood samples.

Figure 5B:
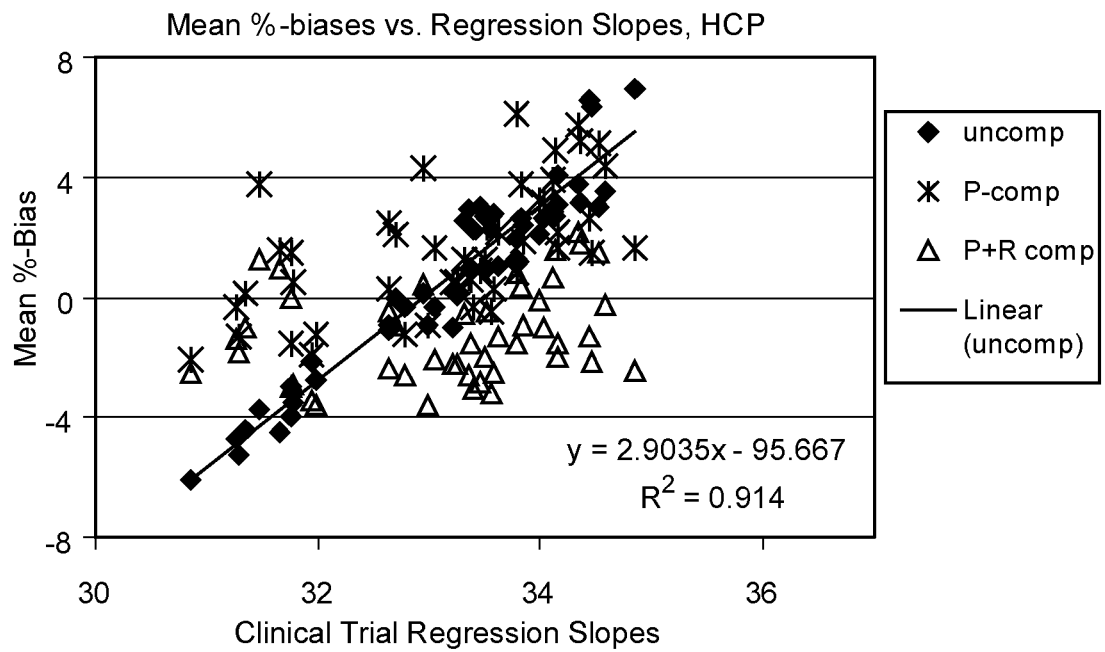
FIG. 5B shows the correlation of the mean percent bias of multiple individual test sensor lots to the regression slope for output currents versus reference glucose concentration for each lot in HCP testing.

FIG. 5B shows the correlation of the mean percent bias of multiple individual test sensor lots to the regression slope for output currents versus reference glucose concentration for each lot. While these results are from a HCP test case, the results may be considered to reflect the manufacturing variations between the sensor lots. FIG. 5B established that the lot-to-lot mean percent biases arising from manufacturing variations between the different test sensor lots were from −4% to +7.5% (an approximately 11.5% range). The compensation method including the combination of primary and residual functions reduced the range of percent mean biases originating from manufacturing variations between the different test sensor lots to from −4% to +2%, a range of approximately 6%. Thus, a compensation method including a primary function and at least one residual function may reduce the mean percent bias spread by about 47% (11.5–6/11.5*100) or more for the mean percent biases of determined analyte concentrations attributable to measurement variations between different lots of test sensors. This mean percent bias spread may be obtained when the analysis method implemented by the biosensor system includes a single conversion function, such as a single value of slope and intercept for calibration.

FIG. 5B also establishes that error compensation including both primary and residual functions may increase the measurement performance of a biosensor system beyond that lost in a conventional biosensor system to the manufacturing variations occurring between lots of the test sensors alone. Thus, error compensation including primary and at least one residual function may allow for greater lot-to-lot manufacturing variability of the test sensors while providing the desired measurement performance to the biosensor system.

Figure 5C:
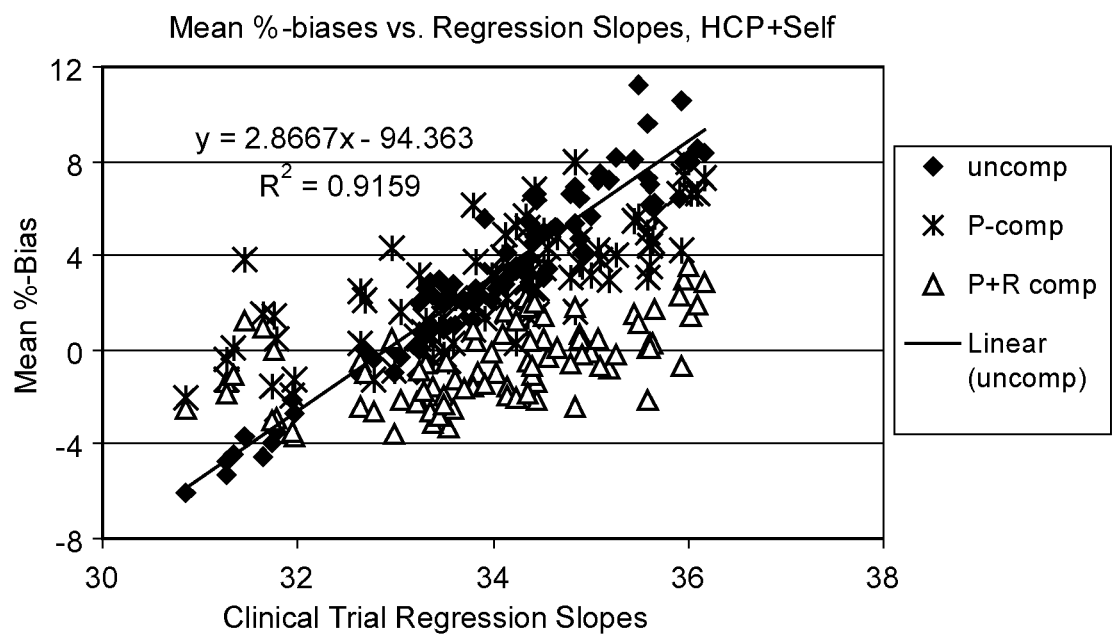
FIG. 5C shows the correlation of the mean percent bias of multiple test sensor lots from HCP and user self-testing test cases after compensation with a primary function, and after compensation with primary and residual functions.

FIG. 5C shows the correlation of the mean percent bias of multiple test sensor lots from HCP and user self-testing test cases after compensation with a primary function, and after compensation with primary and residual functions. In relation to FIG. 5B, the addition of the self-testing test cases should decrease measurement performance as in addition to manufacturing variation error, analysis error from self-testing is being added to the determined analyte concentrations. This effect may be seen in the increase of the lot-to-lot mean percent bias from the prior −4% to +7.5% range of FIG. 5B to the −6% to +12% range observed in FIG. 5C. Thus, the approximately 11.5% spread of FIG. 5B attributable to manufacturing variation error increased to approximately 18% for the combined error attributable to manufacturing variations and user self-testing. The compensation method including the combination of primary and at least one residual function reduced the mean percent biases originating from manufacturing variations and user self-testing to from −4% to +4%, an approximately 8% spread. Thus, a compensation method including a primary function and at least one residual function may reduce the mean percent bias spread of analyses performed with multiple test sensors from multiple test sensor lots under user self-testing conditions to within about ±12%, preferably to within about ±8%, and more preferably to within about ±4%. This mean percent bias spread may be obtained when the analysis method implemented by the biosensor system includes a single conversion function, such as a single value of slope and intercept for calibration.

Figure 5D:
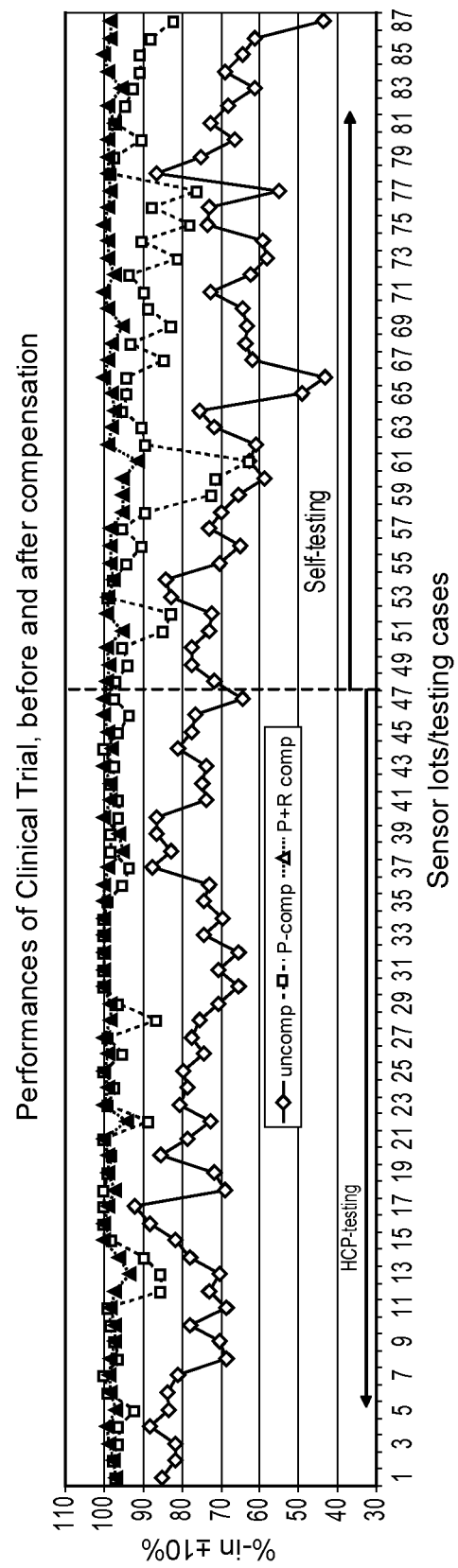
FIG. 5D shows the percent of the analyte determinations having a percent bias limit within a ±10% percent bias limit for each test sensor lot under HCP and self-testing test cases.

FIG. 5D shows the percent of the analyte determinations having a percent bias limit within ±10% for each test sensor lot under HCP and self-testing test cases. The percent biases from the uncompensated analyses of each lot swing widely (between about 40% and about 90%), especially for the self-testing test cases. In contrast, only about 3 of the approximately 87 lots of test sensors fell outside of the 95% within ±10% percent bias limit when the individual analyses were compensated with a primary and at least one residual function.

The compensation method including a primary function and at least one residual function also may improve the measurement performance for analyses including errors arising from manufacturing variation attributable to changes in the activity of the reagents during storage. Bottles containing about 50 test sensors each were taken from each of seven test sensor lots, and placed in storage for about two and four weeks at about 50° C. Bottles containing about 50 test sensors each also were taken from each of seven test sensor lots, and placed in storage for about two and four weeks at about −20° C. for comparison purposes. Two weeks of accelerated aging at about 50° C. represents about 24 months of retail shelf storage while four weeks of accelerated aging at about 50° C. represents about 36 months of retail shelf storage.

The 50° C. stored accelerated aging test sensors and the −20° C. stored comparison test sensors were then used to analyze whole blood samples containing about 58, 172, 342, or 512 mg/dL glucose at a 42% hematocrit level under the controlled environment of a laboratory. Additional accelerated aging and comparison test sensors were then used to develop a residual function to describe operating condition errors.

Glucose concentration values were then determined with a biosensor system for the samples without primary or residual compensation and with primary and residual compensation. The percent bias differences between the accelerated aging and the comparison test sensors are shown in Table 5, below, for the two week period and in Table 6, below, for the four week period.

TABLE 5

| | Un-comp [(+50° C.) − (−20° C.)] | | | | P + R comp [(+50° C.) − (−20° C.)] | | | |
|---|---|---|---|---|---|---|---|---|
| Lot # | 58 mg/dL | 172 | 342 | 513 | 58 | 172 | 342 | 513 |
| 1 | −2.9 | −2.7 | −3.9 | −7.5 | −0.1 | −1.1 | 0.0 | −3.1 |
| 2 | −1.2 | −3.4 | −1.4 | −4.1 | 1.2 | −1.4 | −0.4 | −1.1 |
| 3 | −1.6 | −2.2 | −3.3 | −5.6 | 1.2 | 0.3 | −0.2 | −4.1 |
| 4 | 0.0 | 2.6 | −1.8 | −4.6 | 0.6 | 2.0 | 1.7 | −2.1 |
| 5 | −3.1 | −2.9 | −3.1 | −6.1 | 1.9 | −1.3 | −1.9 | −5.0 |
| 6 | −1.2 | −4.3 | −5.3 | −6.5 | 2.7 | −0.4 | −1.8 | −5.0 |
| 7 | −4.7 | −5.3 | −4.6 | −7.3 | 1.4 | −1.4 | −2.3 | −2.2 |
| Ave | −2.1 | −2.6 | −3.4 | −6.0 | 1.3 | −0.5 | −0.7 | −3.2 |
| SD | 1.5 | 2.5 | 1.4 | 1.3 | 0.9 | 1.2 | 1.4 | 1.5 |

TABLE 6

| | Un-comp [(+50° C.) − (−20° C.)] | | | | P + R comp [(+50° C.) − (−20° C.)] | | | |
|---|---|---|---|---|---|---|---|---|
| Lot # | 59 mg/dL | 173 | 344 | 500 | 59 | 173 | 344 | 500 |
| 1 | −3.3 | −3.0 | −5.7 | −4.8 | 2.1 | 0.6 | −0.8 | −2.3 |
| 2 | −3.4 | −5.2 | −2.4 | −4.4 | 1.7 | −0.4 | 1.2 | −1.6 |
| 3 | −1.7 | −4.4 | −7.9 | −6.9 | 0.5 | −0.3 | −3.1 | −7.4 |
| 4 | −1.5 | −4.1 | −6.2 | −6.2 | 2.2 | −0.3 | −0.8 | −2.8 |
| 5 | −1.8 | −1.2 | −6.4 | −4.4 | 3.4 | 1.9 | −3.2 | −2.6 |
| 6 | −1.5 | −5.8 | −2.5 | −11.8 | 2.4 | −2.5 | 2.4 | −6.7 |
| 7 | −2.2 | −0.4 | −5.0 | −2.1 | 1.0 | 1.8 | −1.9 | −1.9 |
| Ave | −2.2 | −3.5 | −5.2 | −5.8 | 1.9 | 0.1 | −0.9 | −3.6 |
| SD | 0.8 | 2.0 | 2.0 | 3.1 | 1.0 | 1.5 | 2.1 | 2.4 |

The results obtained from the biosensor system in Table 5 and in Table 6 established that a compensation method including a primary and at least one residual function may provide an average percent bias difference between −20° C. stored and 50° C. stored test sensors of ±5% or less for test sensors from at least seven different lots stored for up to four weeks, which translates into about 36 months of retail shelf storage before use.

Biosensor systems having the ability to generate additional output values external to those from the analyte or from the mediator responsive to the analyte also may benefit from the previously described method of error compensation. Systems of this type generally use the additional output value or values to compensate for interferents and other contributors by subtracting the additional output value or values from the analyte responsive output signal in some way. Error parameters may be extracted directly or indirectly from the output signal of the analysis and/or obtained independently from the output signal. Thus, the additional output values external to those from the analyte or from the mediator responsive to the analyte may be used to form terms, such as those described in Intl. Pub. No. WO 2009/108239, filed Dec. 6, 2008, entitled "Slope-Based Compensation," and the like. Both types of terms may be used to form primary and residual functions.

Figure 6A:
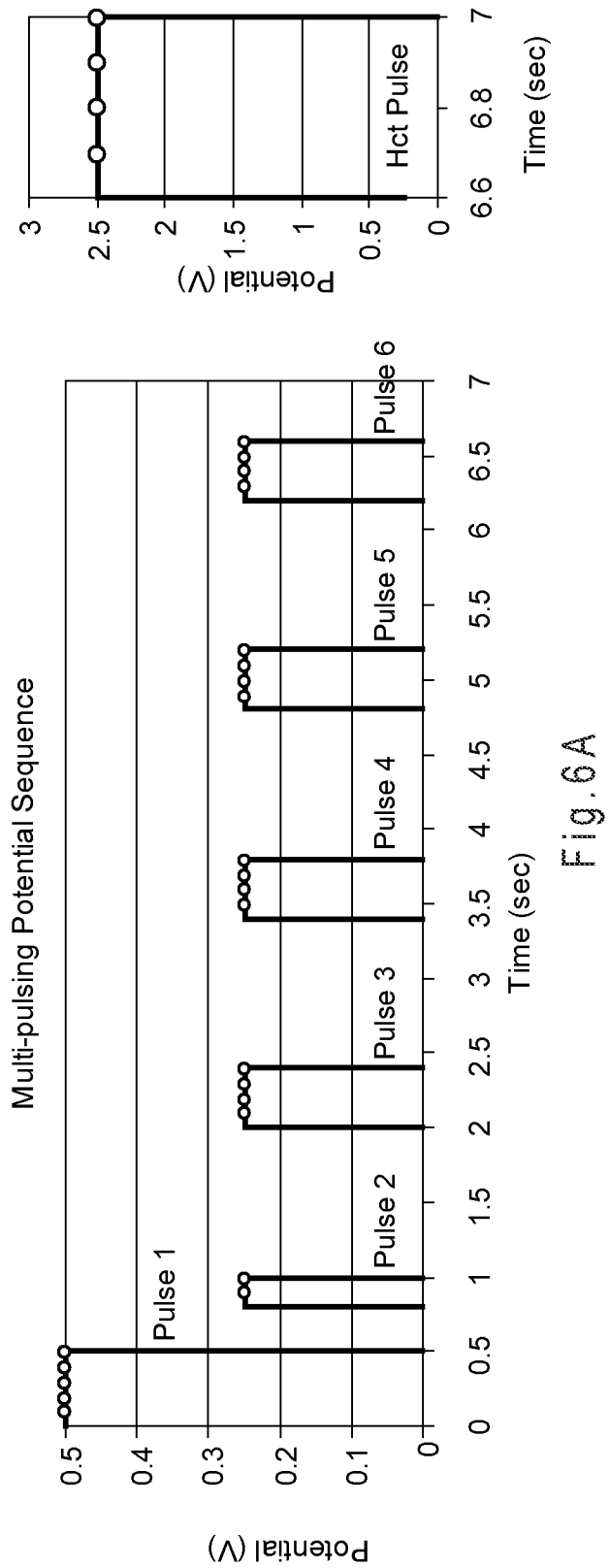
FIG. 6A represents a gated pulse sequence where the input signal applied to the working and counter electrodes includes multiple pulses, and where a second input signal is applied to an additional electrode to generate a secondary output signal.

FIG. 6A represents a gated pulse sequence where the input signal applied to the working and counter electrodes includes multiple pulses, and where a second input signal is applied to an additional electrode to generate a secondary output signal. The input signal applied to the additional electrode was applied after the completion of the analytic input signal applied between the working and counter electrodes, but could be applied at other times. The analytic input signal included six excitation pulses. The input signal applied to the additional electrode included a seventh higher voltage pulse. The solid lines describe the substantially constant input potentials, while the superimposed dots indicate times of taking current measurements. This input signal was applied to multiple test sensors used to determine the glucose concentration of whole blood from multiple internal clinical studies.

The excitations of the analytic input signal of FIG. 6A included pulse-widths of about 0.2, about 0.4, and about 0.5 seconds. While other pulse-widths may be used, pulse widths from about 0.1 to about 0.5 seconds are preferred. Pulse-widths greater than 2 seconds are less preferred. The analytic excitations are separated by relaxations of about 0.5 and about 1 second and were provided by open circuits. While other relaxation-widths may be used, relaxation-widths from about 0.3 to about 1.5 seconds are preferred. The relaxation-width directly preceding the excitation including the current measurement from which the concentration of the analyte is determined is preferably less than 1.5 second. Relaxation-widths greater than 5 seconds are less preferred. In addition to open circuits, relaxations may be provided by other methods that do not apply a potential that appreciably causes the analyte and/or mediator to undergo an electrochemical redox reaction. Preferably, the application of the analytic input signal and the measurement of the associated output currents from the sample are complete in seven seconds or less.

A secondary output signal in the form of a current from an additional electrode may be considered an error parameter describing the hematocrit content of a whole blood sample. The hematocrit content of the sample may be considered an error parameter because an error in concentration values may arise from performing an analysis at a hematocrit content other than that at which the reference correlation was determined. The hematocrit content of the sample may be determined from any source, such as an electrode, calculated estimates, and the like.

The method of error compensation was applied including a conversion function in combination with a primary compensation and a residual compensation as follows:

$$G_{comp}=i_5/[S_{cal}*(1+P+WC*R)],$$

where $G_{comp}$ is the compensated analyte (glucose) concentration of the sample, $i_5$ is the last current value from the fifth excitation pulse as represented in FIG. 6A, $S_{cal}$ is the slope from the reference correlation equation, P is the primary function, WC is a weighing coefficient, and R is a first residual function. Multiple regressions and term exclusions were performed to determine the values for the residual function presented in Table 7, below.

TABLE 7

| Terms | Weighing Coefficient | Coefficient Standard Error | T-value | p-value |
|---|---|---|---|---|
| Constant | 4.4084 | 0.5267 | 8.37 | 0.000 |
| R4/3 | 5.6831 | 0.4293 | 13.24 | 0.000 |
| R5/4 | −5.1348 | 0.5713 | −8.99 | 0.000 |
| R5/3 | −4.2282 | 0.3167 | −13.35 | 0.000 |
| R6/5 | −7.9709 | 0.7639 | −10.43 | 0.000 |
| R6/4 | 7.4002 | 0.6811 | 10.86 | 0.000 |
| $i_{7\_Hct} * G_{raw}$ | 0.00001077 | 0.00000049 | 22.01 | 0.000 |
| $R32 * G_{raw}$ | −0.00158063 | 0.00006795 | −23.26 | 0.000 |
| $R43 * G_{raw}$ | −0.018626 | 0.001039 | −17.93 | 0.000 |
| $R54 * G_{raw}$ | −0.044513 | 0.003521 | −12.64 | 0.000 |
| $R53 * G_{raw}$ | 0.0197795 | 0.0009983 | 19.81 | 0.000 |
| $R65 * G_{raw}$ | 0.046341 | 0.003450 | 13.43 | 0.000 |
| T * R32 | 0.0014813 | 0.0002473 | 5.99 | 0.000 |
| T * R54 | 0.030060 | 0.003713 | 8.10 | 0.000 |
| T * R64 | −0.037374 | 0.003893 | −9.60 | 0.000 |
| $i_{7\_Hct} * R43$ | −0.0014528 | 0.0001257 | −11.56 | 0.000 |
| $i_{7\_Hct} * R53$ | 0.00078356 | 0.00007417 | 10.56 | 0.000 |
| $i_{7\_Hct} * R65$ | 0.00066095 | 0.00006537 | 10.11 | 0.000 |
| $i_{7\_Hct} * R54 * G_{raw}$ | 0.00001748 | 0.00000138 | 12.69 | 0.000 |
| $i_{7\_Hct} * R65 * G_{raw}$ | −0.00002892 | 0.00000172 | −16.84 | 0.000 |

S = 0.0371099
R-Sq = 41.4%
R-Sq(adj) = 41.3%

A complex index function was used as a primary function to compensate the correlation slope $S_{cal}$. A first residual function was used to compensate errors not compensated for by the primary function. The primary and first residual functions were determined with their appropriate weighing coefficients as follows:

Primary Function=17.5252−0.012154*'$i_{7\_Hct}$'−
0.0258*'R3/2'−15.057*'R5/4'−20.04*'R6/5'+
16.318*'R6/4'−5.1e−7*'$i_{7\_Hct}$*$G_{raw}$'+
0.0029343*'R43*$G_{raw}$'+0.01512*'R54*$G_{raw}$'−
0.0191066*'R65*$G_{raw}$'−1.55e−6*'T*$i_{7\_Hct}$'+
0.030154*'T*R54'−0.006368*'T*R53'−9.476e−
4*'$i_{7\_Hct}$*R43'+0.011803*'$i_{7\_Hct}$*R54'+8.112e−
4*'$i_{7\_Hct}$*R53'+0.013868*'$i_{7\_Hct}$*R65'−
0.01303*'$i_{7\_Hct}$*R64'−9.1e−
6*'$i_{7\_Hct}$*R54*$G_{raw}$'+1.02e−
5*'$i_{7\_Hct}$*R65*$G_{raw}$';

First Residual Function=4.4084+5.683*'R4/3'−
5.1348*'R5/4'−4.2282*'R5/3'−7.971*'R6/5'+
7.40*'R6/4'+1.08e−5*'$i_{7\_Hct}$*$G_{raw}$'−
0.0015806*'R32*$G_{raw}$'−0.018626*'R43*$G_{raw}$'−
0.044513*'R54*$G_{raw}$'+0.01978*'R53*$G_{raw}$'+
0.04634*'R65*$G_{raw}$'+0.001481*'T*R32'+
0.03006*'T*R54'−0.03737*'T*R64'−
0.001453*'$i_{7\_Hct}$*R43'+7.836e−
4*'$i_{7\_Hct}$*R53'+6.61e−4*'$i_{7\_Hct}$*R65'+1.75e−
5*'$i_{7\_Hct}$*R54*$G_{raw}$'−2.89e−
5*'$i_{7\_Hct}$*R65*$G_{raw}$';

where $i_{7\_Hct}$ is the current from hematocrit sensing electrode at 7 sec, T is the measurement device temperature, and R3/2, R4/3, R5/4, R6/5, R5/3, and R6/4 are inter-pulse ratio indices having the general format of the last current of a later intime pulse divided by the last current of an earlier in time pulse. Additional information may be found in Intl. Pub. No. WO2010/0776690 regarding index functions and intermediate signal value ratios.

Figure 6B:
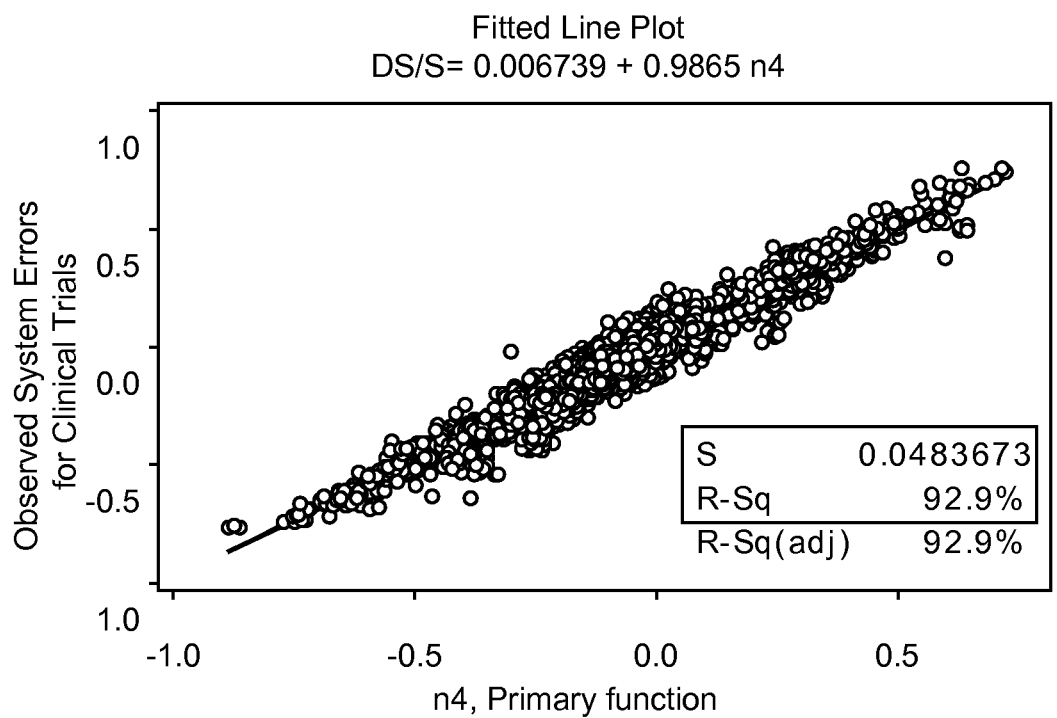
FIG. 6B is the correlation plot between the total errors of data from multiple internal clinical studies and the primary function values.
Figure 6C:
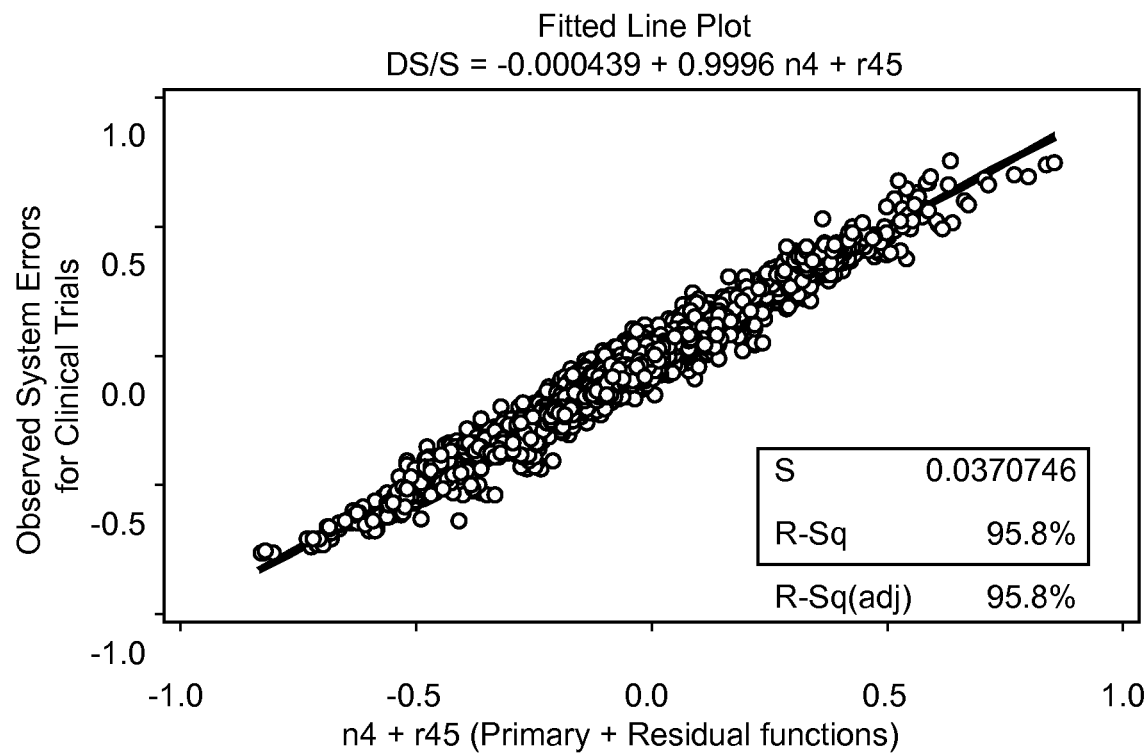
FIG. 6C shows the correlation plot between the total errors of the same data versus the combined values of primary and first residual functions.

FIG. 6B is the correlation plot between the total errors of data from multiple internal clinical studies and the primary function values, which provided a correlation coefficient of 92.9%. FIG. 6C shows the correlation plot between the total errors of the same data versus the combined values of primary and first residual functions. The overall correlation coefficient increases from 92.9% to 95.8% by adding the first residual function values. An improvement in measurement performance also can be seen in the reduction of the SD value from 0.04836 to 0.03707 with the addition of the first residual function.

Residual function compensation also may be used when a test sensor is filled with sample twice, such as when the first filling is insufficient and additional sample is added a short time later. When an underfill condition is detected, the beginning of the analysis may be delayed until the test sensor is filled again. The error associated with this double filling process is first compensated by the primary function. The remaining double filling errors may then be compensated by a residual function.

In the case of a 4-electrode sensor, where on entry to the test sensor the sample crosses a first electrode (A) before a second (B), the second (B) before a third (C), and the third (C) before a fourth (D), the time required for the sample to reach between electrodes (B) and (C) and the time for reaching between electrodes (C) and (D) may be expressed as BC and CD respectively.

The BC time is normally associated with low volume underfill (approximately 0.3 uL as opposed to the full-fill volume of 0.5 uL) while the CD time is normally associated with the high volume underfill (approximately 0.5 uL).

These two events are substantially mutually exclusive and independent of each other and each may have a different residual function after the same primary function. The general compensation functions may be represented as follows:

$$BC\ errors = primary + WC_{BC} * residual_{BC}$$

$$CD\ errors = primary + WC_{CD} * residual_{CD}$$

Thus, in accord with the general equation $G_{compBC}=i_5/[S_{cal}*(1+P+WC*R_{BC})]$ or $G_{compCD}=i_5/[S_{cal}*(1+P+WC*R_{CD})]$, primary, first residual$_{BC}$, and first residual$_{CD}$ functions were determined as follows:

Primary Function=32.705−0.025411*'7'−
31.686*'R5/4'−33.37*'R6/5'+31.386*'R6/4'+
3e−7*'7*G'−3.9021e−4*'R32*G'+
0.0029771*'R43*G'−0.0029786*'R54*G'+
8.09e−6*'T*7'−0.015815*'T*R43'+
0.14909*'T*R54'−0.18932*'T*R65'+
0.060677*'T*R64'+0.023466*'7*R54'+
0.027866*'7*R65'−0.025683*'7*R64';

First Residual Function$_{BC}$=16.995+0.001944*'7'+
90.03*'R5/4'−17.69*'R5/3'−127.72*'R6/5'+
37.924*'R6/4'−5.77e−6*'AE*7'−
0.0035248*'R43*G'+0.004296*'R64*G'+
0.9513*'T*R43'−4.508*'T*R54'+
3.5624*'T*R65'−0.0019169*'7*R43'−
0.1322*'AE*R54'+0.14019*'AE*R65'−
0.003643*'AC*R65'; and First Residual Function$_{CD}$=3.1062+0.011148*'7'+
20.345*'R3/2'−143.8*'R4/3'+125.96*'R5/4'+
0.032094*'R54*G'−0.008077*'R53*G'−
0.024023*'R65*G'+7.43e−5*'T*7'−
0.8642*'T*R32'+6.1618*'T*R43'−
5.5315*'T*R54'−0.012701*'7*R54'−

0.014974*'7*R65'+0.014655*'7*R64'+2.872e−5*'AC*7'−0.052885*'AC*R43'.

Figure 6D:
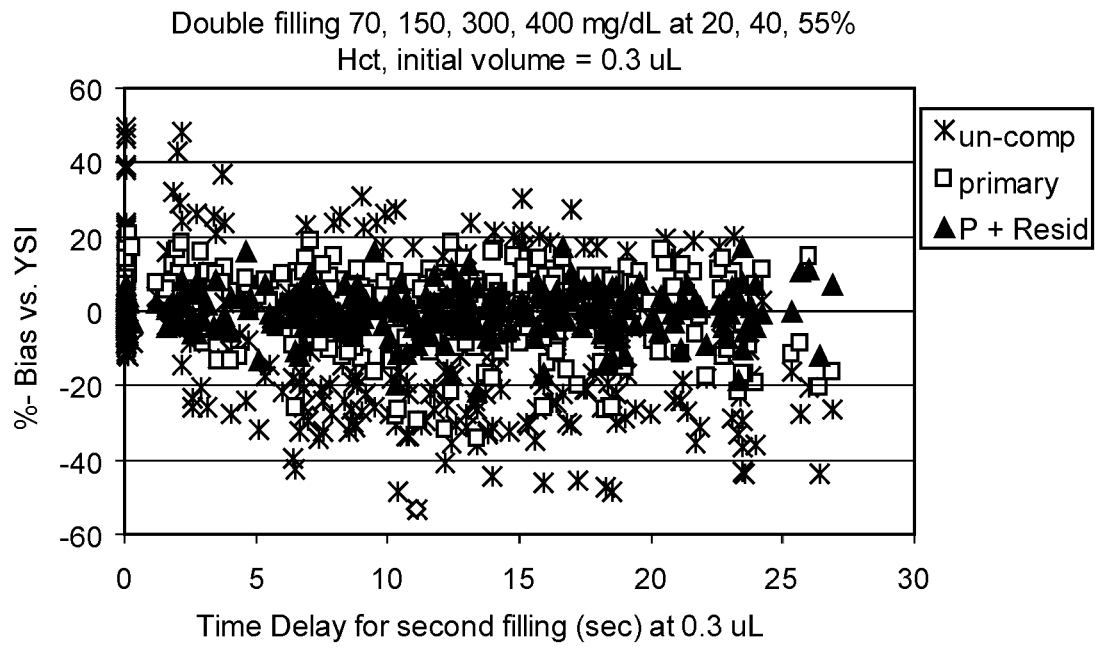
FIG. 6D depicts the percent biases as a function of the time using a BC residual.
Figure 6E:
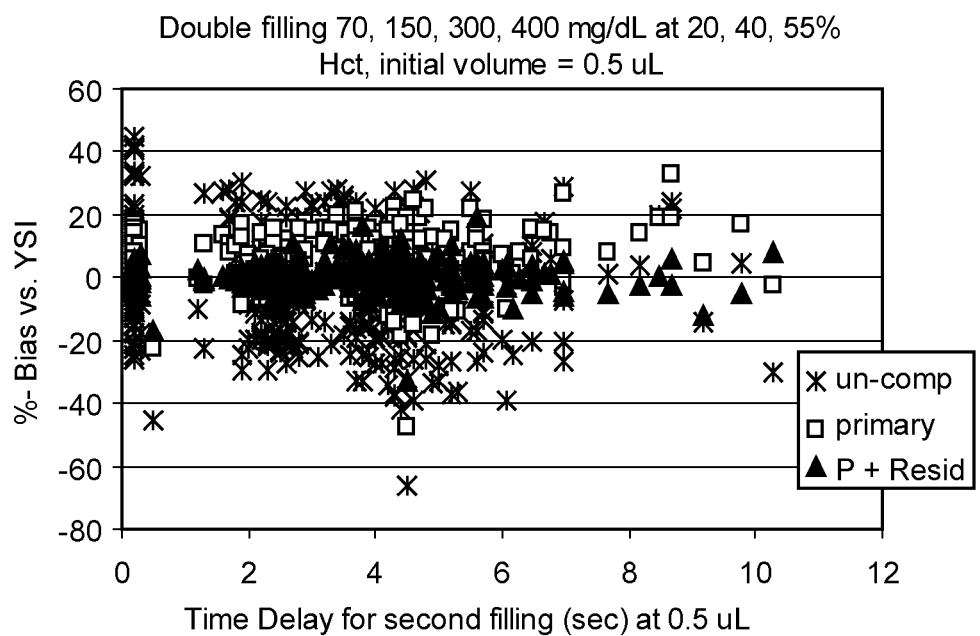
FIG. 6E depicts the percent biases as a function of the time using a CD residual.

In this manner, a method of error compensation may include a single primary function, which is used in combination with different first residual functions to provide two or more modes of compensation to the biosensor system. FIG. 6D depicts the percent biases as a function of the time using the BC residual, and FIG. 6E depicts the percent biases as a function of the time using the CD residual. For both the BC and CD first residuals, the primary function compensates for environmental and physical sample characteristic error contributors, including temperature and hematocrit. The operating condition errors associated with the under-filling and refilling process, forms of operating condition errors, are compensated by the first residual function for each underfill circumstance.

TABLE 8

|  | Un-comp | Primary only | Primary ± Residual | | |
| --- | --- | --- | --- | --- | --- |
| Volume | ±10% | ±10% | ±10% | ±12.5% | ±15% |
| BC (0.3 µL) | 30% | 87% | 92.0% | 95.7% | 97.0% |
| CD (0.5 µL) | 33% | 65% | 95.7% | 98.7% | 98.7% |

Table 8, above, provides additional data describing the compensation results from test sensors underfilled at the approximately 0.3 µL and 0.5 µL volumes that were then fully filled after the initial under-fill. Thus, while completely filled by the second filling, the BC test sensors were originally filled with about 0.3 µL of whole blood, while the CD test sensors were originally filled with about 0.5 µL of whole blood. While only about 30% of the uncompensated reading fell within the ±10% percent bias limit, the combination of primary and residual compensation placed over 90% of the data within the desired ±10% limit. Thus, a compensation method including a primary function and at least one residual function may place 90% or more of the determined analyte concentrations within a ±10% percent bias limit when the test sensors are initially underfilled and then fully filled by users.

Figure 7A:
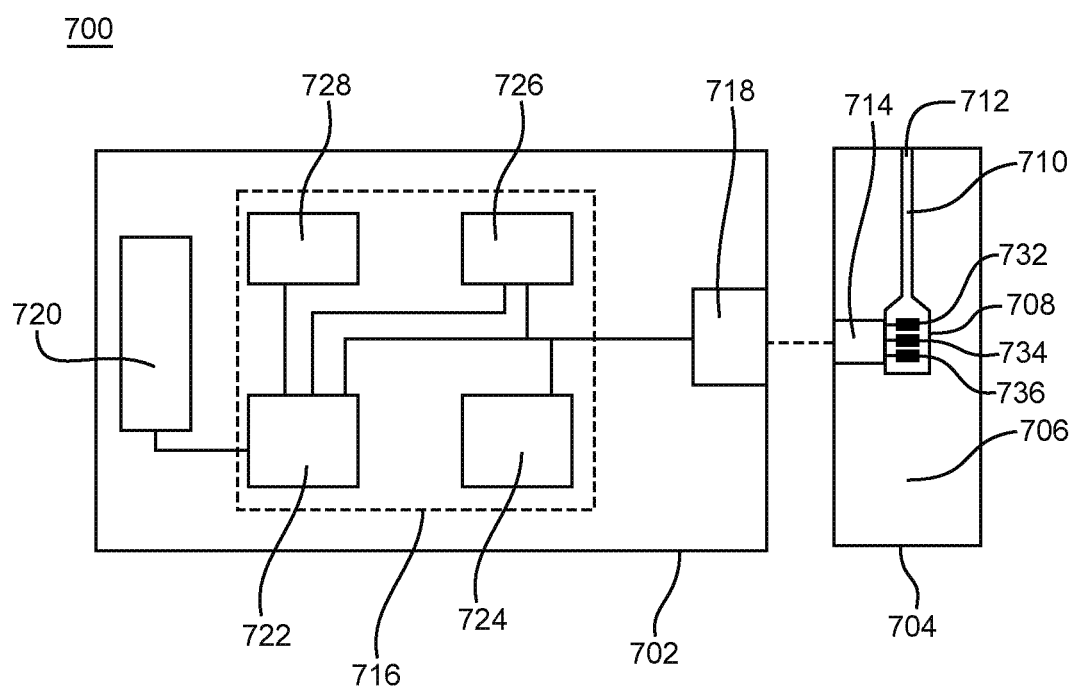
FIG. 7A depicts a schematic representation of a biosensor system that determines an analyte concentration in a sample of a biological fluid.

FIG. 7A depicts a schematic representation of a biosensor system 700 that determines an analyte concentration in a sample of a biological fluid. Biosensor system 700 includes a measurement device 702 and a test sensor 704, which may be implemented in any analytical instrument, including a bench-top device, a portable or hand-held device, or the like. The measurement device 702 and the test sensor 704 may be adapted to implement an electrochemical sensor system, an optical sensor system, a combination thereof, or the like. The biosensor system 700 determines the analyte concentration of the sample from a method of error compensation including at least one conversion function, at least one primary compensation, at least one residual compensation, and the output signal. The method of error compensation may improve the measurement performance of the biosensor system 700 in determining the analyte concentration of the sample. The biosensor system 700 may be utilized to determine analyte concentrations, including those of glucose, uric acid, lactate, cholesterol, bilirubin, and the like. While a particular configuration is shown, the biosensor system 700 may have other configurations, including those with additional components.

The test sensor 704 has a base 706 that forms a reservoir 708 and a channel 710 with an opening 712. The reservoir 708 and the channel 710 may be covered by a lid with a vent. The reservoir 708 defines a partially-enclosed volume. The reservoir 708 may contain a composition that assists in retaining a liquid sample such as water-swellable polymers or porous polymer matrices. Reagents may be deposited in the reservoir 708 and/or the channel 710. The reagents may include one or more enzymes, binders, mediators, and like species. The reagents may include a chemical indicator for an optical system. The test sensor 704 may have other configurations.

In an optical sensor system, the sample interface 714 has an optical portal or aperture for viewing the sample. The optical portal may be covered by an essentially transparent material. The sample interface 714 may have optical portals on opposite sides of the reservoir 708.

In an electrochemical system, the sample interface 714 has conductors connected to a working electrode 732 and a counter electrode 734 from which the analytic output signal may be measured. The sample interface 714 also may include conductors connected to one or more additional electrodes 736 from which secondary output signals may be measured. The electrodes may be substantially in the same plane or in more than one plane. The electrodes may be disposed on a surface of the base 706 that forms the reservoir 708. The electrodes may extend or project into the reservoir 708. A dielectric layer may partially cover the conductors and/or the electrodes. The sample interface 714 may have other electrodes and conductors.

The measurement device 702 includes electrical circuitry 716 connected to a sensor interface 718 and a display 720. The electrical circuitry 716 includes a processor 722 connected to a signal generator 724, an optional temperature sensor 726, and a storage medium 728.

The signal generator 724 provides an electrical input signal to the sensor interface 718 in response to the processor 722. In optical systems, the electrical input signal may be used to operate or control the detector and light source in the sensor interface 718. In electrochemical systems, the electrical input signal may be transmitted by the sensor interface 718 to the sample interface 714 to apply the electrical input signal to the sample of the biological fluid. The electrical input signal may be a potential or current and may be constant, variable, or a combination thereof, such as when an AC signal is applied with a DC signal offset. The electrical input signal may be applied as a single pulse or in multiple pulses, sequences, or cycles. The signal generator 724 also may record an output signal from the sensor interface as a generator-recorder.

The optional temperature sensor 726 determines the temperature of the sample in the reservoir of the test sensor 704. The temperature of the sample may be measured, calculated from the output signal, or assumed to be the same or similar to a measurement of the ambient temperature or the temperature of a device implementing the biosensor system. The temperature may be measured using a thermister, thermometer, or other temperature sensing device. Other techniques may be used to determine the sample temperature.

The storage medium 728 may be a magnetic, optical, or semiconductor memory, another storage device, or the like. The storage medium 728 may be a fixed memory device, a removable memory device, such as a memory card, remotely accessed, or the like.

The processor 722 implements the analyte analysis and data treatment using computer readable software code and data stored in the storage medium 728. The processor 722 may start the analyte analysis in response to the presence of the test sensor 704 at the sensor interface 718, the application of a sample to the test sensor 704, in response to user input, or the like. The processor 722 directs the signal generator 724 to provide the electrical input signal to the sensor interface 718. The processor 722 receives the sample temperature from the temperature sensor 726. The processor 722 receives the output signal from the sensor interface 718. The output signal is generated in response to the reaction of the analyte in the sample. The output signal may be generated using an optical system, an electrochemical system, or the like. The processor 722 determines analyte concentrations from output signals using a compensation method including primary and at least one residual function as previously discussed. The results of the analyte analysis may be output to the display 720 and may be stored in the storage medium 728.

The correlation equations between analyte concentrations and output signals may be represented graphically, mathematically, a combination thereof, or the like. A correlation equation may include one or more index functions. Correlation equations may be represented by a program number (PNA) table, another look-up table, or the like that is stored in the storage medium 728. Constants and weighing coefficients also may be stored in the storage medium 728. Instructions regarding implementation of the analyte analysis may be provided by the computer readable software code stored in the storage medium 728. The code may be object code or any other code describing or controlling the functionality described herein. The data from the analyte analysis may be subjected to one or more data treatments, including the determination of decay rates, K constants, ratios, functions, and the like in the processor 722.

In electrochemical systems, the sensor interface 718 has contacts that connect or electrically communicate with the conductors in the sample interface 714 of the test sensor 704. The sensor interface 718 transmits the electrical input signal from the signal generator 724 through the contacts to the connectors in the sample interface 714. The sensor interface 718 also transmits the output signal from the sample through the contacts to the processor 722 and/or signal generator 724.

In light-absorption and light-generated optical systems, the sensor interface 718 includes a detector that collects and measures light. The detector receives light from the liquid sensor through the optical portal in the sample interface 714. In a light-absorption optical system, the sensor interface 718 also includes a light source such as a laser, a light emitting diode, or the like. The incident beam may have a wavelength selected for absorption by the reaction product. The sensor interface 718 directs an incident beam from the light source through the optical portal in the sample interface 714. The detector may be positioned at an angle such as 45° to the optical portal to receive the light reflected back from the sample. The detector may be positioned adjacent to an optical portal on the other side of the sample from the light source to receive light transmitted through the sample. The detector may be positioned in another location to receive reflected and/or transmitted light.

The display 720 may be analog or digital. The display 720 may include a LCD, a LED, an OLED, a vacuum fluorescent, or other display adapted to show a numerical reading. Other displays may be used. The display 720 electrically communicates with the processor 722. The display 720 may be separate from the measurement device 702, such as when in wireless communication with the processor 722. Alternatively, the display 720 may be removed from the measurement device 702, such as when the measurement device 702 electrically communicates with a remote computing device, medication dosing pump, and the like.

In use, a liquid sample for analysis is transferred into the reservoir 708 by introducing the liquid to the opening 712. The liquid sample flows through the channel 710, filling the reservoir 708 while expelling the previously contained air. The liquid sample chemically reacts with the reagents deposited in the channel 710 and/or reservoir 708.

The test sensor 702 is disposed adjacent to the measurement device 702. Adjacent includes positions where the sample interface 714 is in electrical and/or optical communication with the sensor interface 718. Electrical communication includes the transfer of input and/or output signals between contacts in the sensor interface 718 and conductors in the sample interface 714. Optical communication includes the transfer of light between an optical portal in the sample interface 714 and a detector in the sensor interface 718. Optical communication also includes the transfer of light between an optical portal in the sample interface 714 and a light source in the sensor interface 718.

The processor 722 receives the sample temperature from the temperature sensor 726. The processor 722 directs the signal generator 724 to provide an input signal to the sensor interface 718. In an optical system, the sensor interface 718 operates the detector and light source in response to the input signal. In an electrochemical system, the sensor interface 718 provides the input signal to the sample through the sample interface 714. The processor 722 receives the output signal generated in response to the redox reaction of the analyte in the sample as previously discussed.

The processor 722 determines the analyte concentration of the sample. The measurement device adjusts the correlation between analyte concentrations and output signals with through compensation including a primary and at least one residual function. Other compensations and functions also may be implemented by the process or 722.

While various embodiments of the invention have been described, it will be apparent to those of ordinary skill in the art that other embodiments and implementations are possible within the scope of the invention.

What is claimed is:

1. A method of operating a biosensor system for determining an analyte concentration in a biological fluid sample when at least one operating condition error is introduced into an analysis by user self-testing, the method comprising:
    providing a biosensor system in the form of an analytical instrument including
        a measurement device having electrical circuitry communicatively coupled to a processor, a storage medium, a signal generator, and a sensor interface, the processor having instructions and data stored in the storage medium, and
        a test sensor having a base and a sample interface, the base forming a reservoir and a channel with an opening, the base further having a surface on which at least one working electrode and at least one counter electrode are disposed, the reservoir being in electrical or optical communication with the measurement device, the sample interface having conductors connected to the working electrode and the counter electrode;
    determining in a controlled environment, prior to the user self-testing, a primary error of an uncompensated analyte concentration, the primary error being at least 50% of a total error of the uncompensated analyte concentration and including at least one of a temperature error or a hematocrit error; and subsequently and outside the controlled environment, initiating the user self-testing via the biosensor system to determine a compensated analyte concentration, the user self-testing including:

receiving the biological fluid sample in the opening, the biological fluid sample flowing through the channel to fill at least in part the reservoir of the test sensor, introducing the operating condition error during the user self-testing but prior to determining the compensated analyte concentration in the biological fluid sample, in response to receiving the biological fluid sample in the reservoir, generating an input signal, by the processor, from the signal generator, transmitting the input signal by the sensor interface to the sample interface for applying the input signal to the biological fluid sample, in response to the input signal and the uncompensated analyte concentration, receiving and measuring, by the processor, an output signal from the working electrode and the counter electrode of the test sensor, compensating, by the processor, the primary error in the output signal with a primary function, the primary function being in the form of an index function that is determined using error parameter values from an analyte analysis or from a source independent of an analyte responsive output signal, compensating, by the processor, a remaining error of the total error in the output signal with a first residual function, the first residual function compensating the remaining error until errors become random, the remaining error being the operating condition error, determining a compensated output signal based on the compensating of the primary error and the remaining error in the output signal, and determining, by the processor, the compensated analyte concentration in the biological fluid sample from the compensated output signal in which the total error has been reduced by compensating for the primary error and the remaining error.

2. The method of claim 1, further comprising determining at least one reference correlation with a reference instrument in the controlled environment prior to determining the compensated analyte concentration in the biological fluid sample.

3. The method of claim 1, further comprising adjusting the compensation provided by the first residual function with a first weighing coefficient, the first weighing coefficient being responsive to the compensation provided by the primary function.

4. The method of claim 3, further comprising compensating the output signal with a second residual function to determine a further compensated output signal, the second residual function being for further compensating residual errors remaining after application of the first residual function.

5. The method of claim 4, further comprising adjusting the compensation provided by the second residual function with a second weighing coefficient, the second weighing coefficient being responsive to the compensation provided by the first residual function.

6. The method of claim 1, wherein the first residual function compensates at least 5% of the total error in the output signal.

7. The method of claim 1, further comprising determining the first residual function by:

selecting multiple error parameters as potential terms in the first residual function, the error parameters being any value responsive to one or more errors in the output signal;

determining a first exclusion value for the potential terms;

applying an exclusion test responsive to the first exclusion value for the potential terms;

identifying one or more of the potential terms for exclusion from the first residual function; and excluding one or more identified potential terms from the first residual function.

8. The method of claim 1, further comprising:

determining if the test sensor is filled more than once with the biological fluid sample before the output signal is generated; and determining the compensated output signal from a different first residual function if the test sensor is filled more than once.

9. The method of claim 1, wherein the biological fluid sample is a whole blood sample and an analyte of the compensated analyte concentration is glucose, the determining of the compensated analyte concentration in the biological fluid sample from the compensated output signal reducing the slope of a correlation plot representing hematocrit sensitivity in whole blood to ±0.4 or less when the whole blood sample has a hematocrit level from about 30% to about 55%.

10. The method of claim 1, wherein the compensated analyte concentration is determined from at least a forty-sample self-testing test case, and wherein the test case has a measurement performance of at least one of at least 85% of the determined uncompensated analyte concentrations being within a ±10% percent bias limit, at least 95% of the determined uncompensated analyte concentrations being within a ±8% percent bias limit, and at least 60% of the determined uncompensated analyte concentrations being within a +5% percent bias limit.

11. The method of claim 1, wherein the compensated analyte concentration is determined from at least a 5,000-sample test case, the test case being at least one of a self-testing test case and a health care professional test case, the test case using test sensors from between two and 45 test-sensor lots, the test case having a measurement performance of at least one of the determined uncompensated analyte concentrations having an average percent bias standard deviation value of less than five, at least 90% of the determined uncompensated analyte concentrations being within a ±10% percent bias, and the determined uncompensated analyte concentrations having a mean percent bias spread within about +12%.

12. The method of claim 1, wherein the compensated analyte concentration lacks at least 60% of the total error of the output signal.

13. The method of claim 1, wherein a mean percent bias of the compensated analyte concentrations determined from the compensated output signal from different lots of test sensors is at least 47% less than a mean percent bias determined from the output signal for uncompensated analyte concentrations determined from the different lots of test sensors.

14. The method of claim 1, further comprising reducing to +5% or less the difference between uncompensated analyte concentrations determined from test sensors stored for four weeks at −20° C. and uncompensated analyte concentrations determined from test sensors stored for four weeks at 50° C.

15. The method of claim 8, wherein 90% or more of the determined uncompensated analyte concentrations are within a +10% percent bias limit when the test sensors are filled more than once with the sample before the output signal is generated.

* * * * *